(12) United States Patent
Hart et al.

(10) Patent No.: US 8,292,853 B2
(45) Date of Patent: Oct. 23, 2012

(54) SELF-SEALING CANNULA HAVING INTEGRATED SEALS

(75) Inventors: Charles C. Hart, Summerville, SC (US); John R. Brustad, Dana Point, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 1343 days.

(21) Appl. No.: 10/807,974

(22) Filed: Mar. 24, 2004

(65) Prior Publication Data

US 2005/0216028 A1    Sep. 29, 2005

(51) Int. Cl.
*A61M 5/178*    (2006.01)
(52) U.S. Cl. ......... 604/167.06; 604/167.01; 604/167.02; 604/167.03; 604/167.04
(58) Field of Classification Search ............. 604/164.01, 604/164.02, 164.03, 164.06, 166.01, 167.01–167.04, 604/167.06
See application file for complete search history.

(56) References Cited

U.S. PATENT DOCUMENTS

| 4,895,346 | A | * | 1/1990 | Steigerwald ............... 251/149.1 |
| 5,141,498 | A | | 8/1992 | Christian |
| 5,346,459 | A | | 9/1994 | Allen |
| 5,454,791 | A | | 10/1995 | Tovey et al. |
| 5,569,205 | A | * | 10/1996 | Hart et al. ................ 604/167.03 |
| 5,752,970 | A | | 5/1998 | Yoon |
| 5,797,888 | A | | 8/1998 | Yoon |
| 5,803,919 | A | * | 9/1998 | Hart et al. ................. 604/167.04 |
| 6,017,328 | A | * | 1/2000 | Fischell et al. ................ 604/180 |
| 6,497,716 | B1 | | 12/2002 | Green et al. |
| 6,520,939 | B2 | * | 2/2003 | Lafontaine ............... 604/167.03 |
| 6,767,340 | B2 | * | 7/2004 | Willis et al. .................... 604/256 |
| 2004/0068232 | A1 | | 4/2004 | Hart et al. |
| 2005/0131349 | A1 | * | 6/2005 | Albrecht et al. ......... 604/167.06 |
| 2005/0165433 | A1 | * | 7/2005 | Haberland et al. ............ 606/167 |

FOREIGN PATENT DOCUMENTS

WO    WO 02/064203 A1    8/2002
WO    WO 03/043683 A1    5/2003

OTHER PUBLICATIONS

International Search Report and Written Opinion of the International Searching Authority dated Sep. 8, 2005 (mailing date), for PCT application No. PCT/US05/005473, Applied Medical Resources.

* cited by examiner

*Primary Examiner* — Bhisma Mehta
(74) *Attorney, Agent, or Firm* — John F. Heal

(57) ABSTRACT

The present invention relates to a surgical access device comprising an elongate tubular member having a working channel and a proximal end and a distal end, a septum seal integrally formed at the distal end of the tubular member, and a zero seal disposed at the distal end of the tubular member and distal to the septum seal, the zero seal being sized and configured to seal when no instrument is in place within the working channel of the tubular member, and the zero seal being coupled to the septum seal The zero seal may be a duckbill seal having opposing lip portions separated by a slit portion. The opposing lip portions are coated with or attached to a soft or occlusive material.

32 Claims, 26 Drawing Sheets

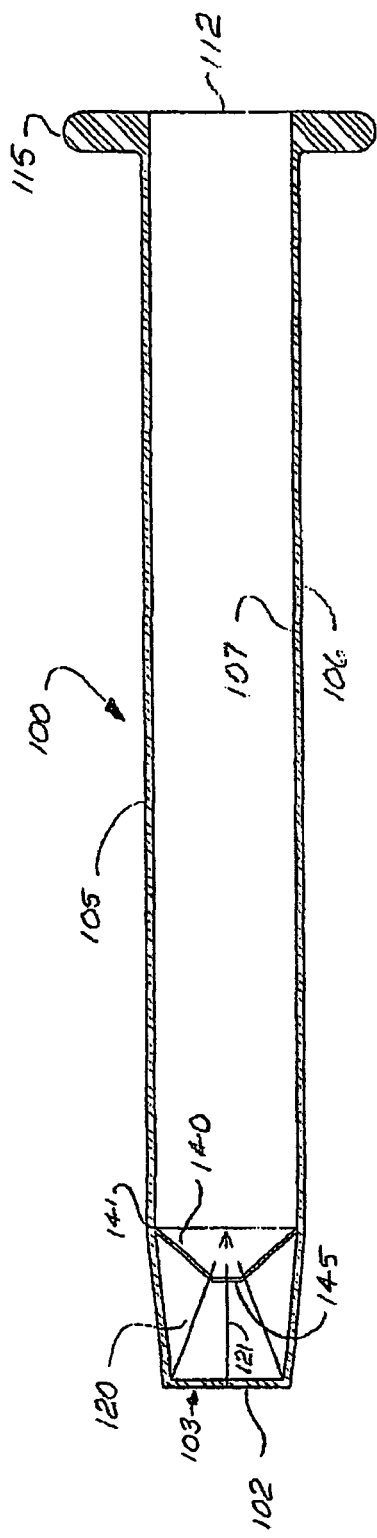
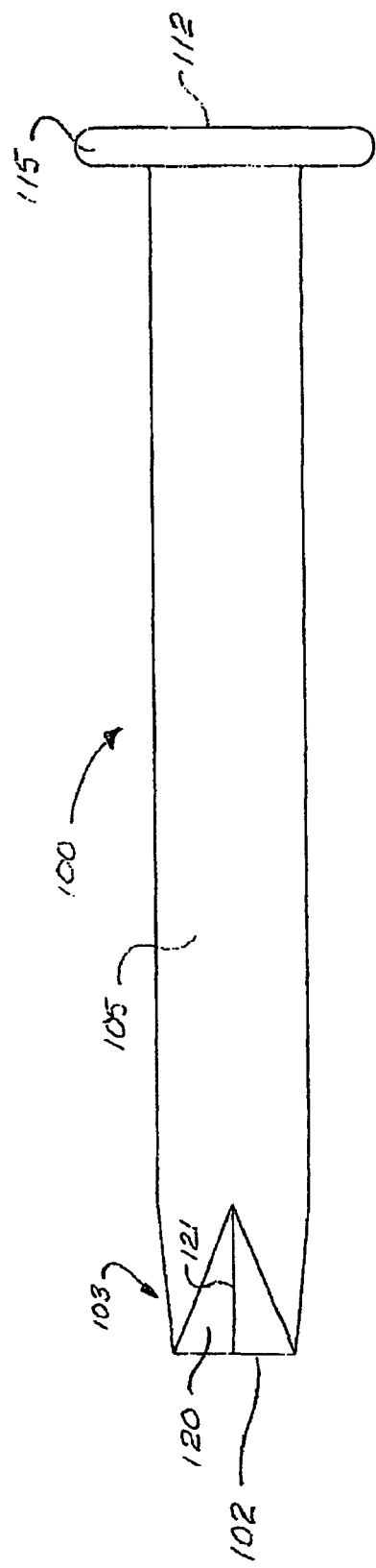
FIG. 6
FIG. 5

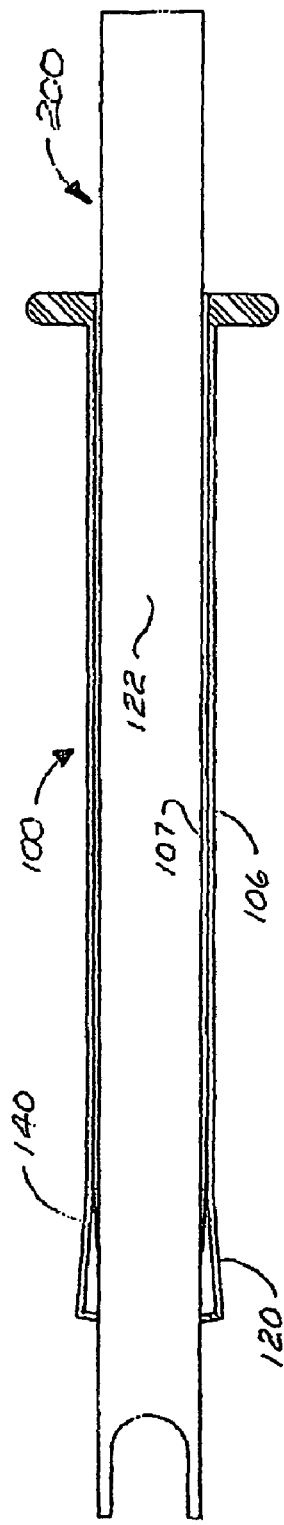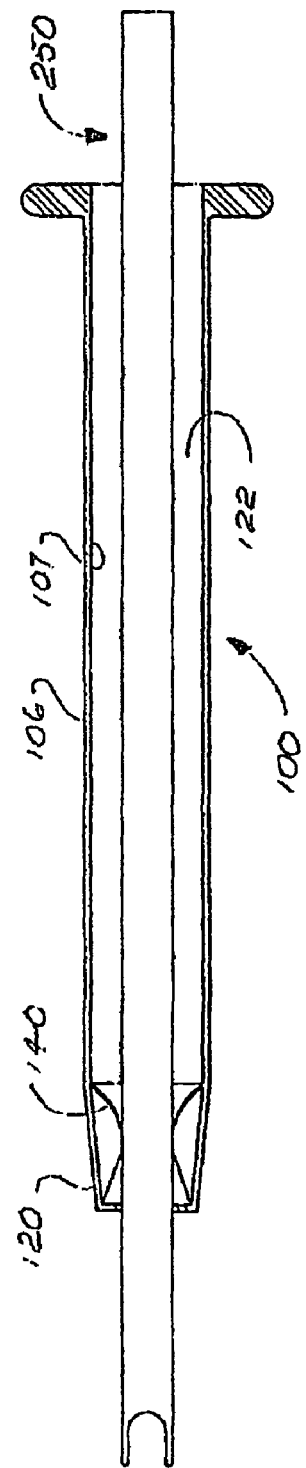
FIG. 7
FIG. 8

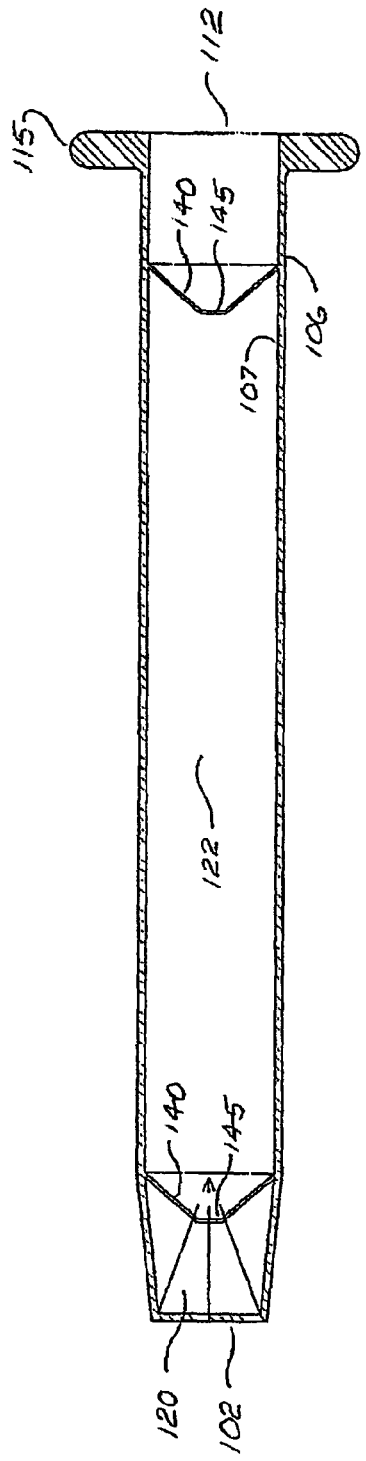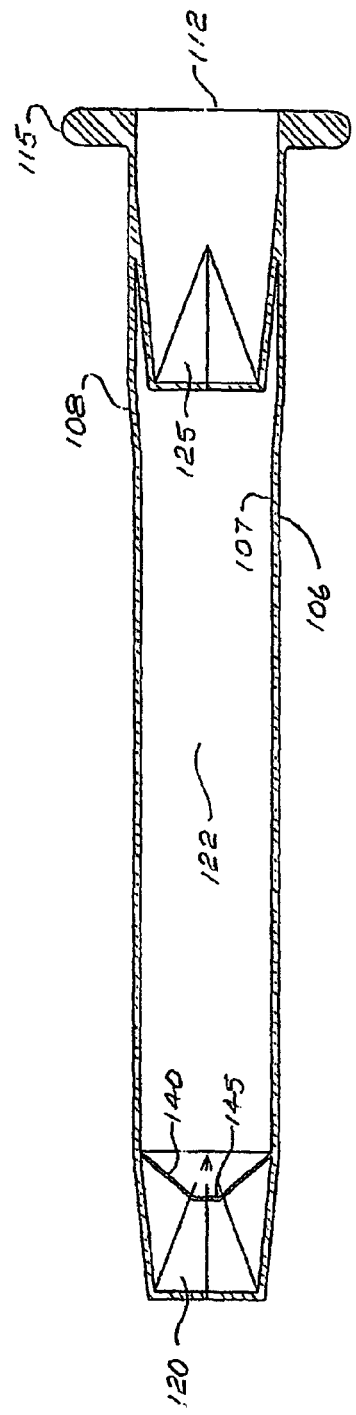
FIG. 14
FIG. 15

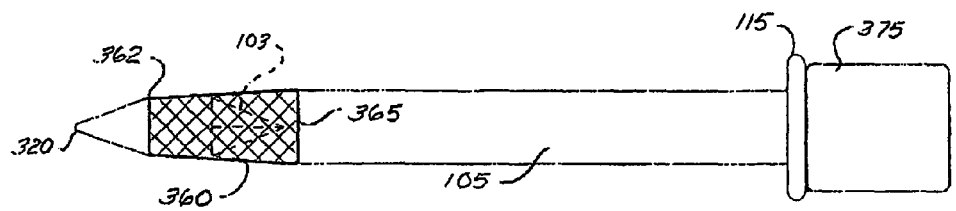
FIG. 23
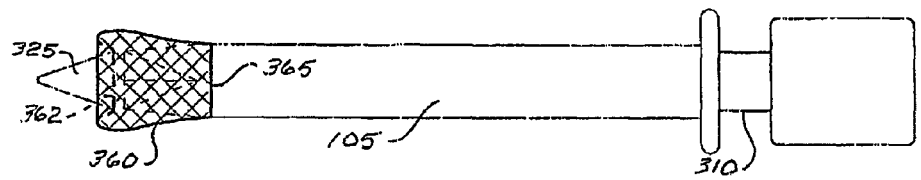
FIG. 24
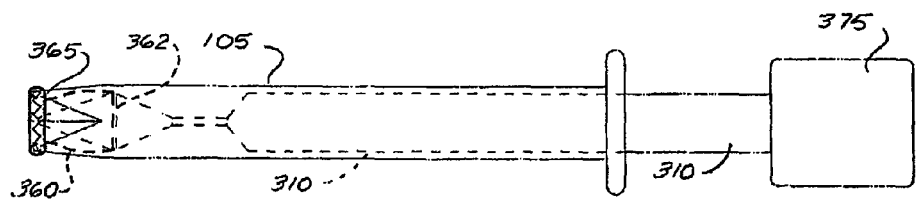
FIG. 25
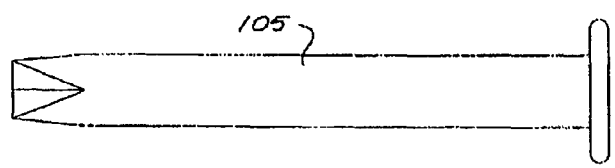
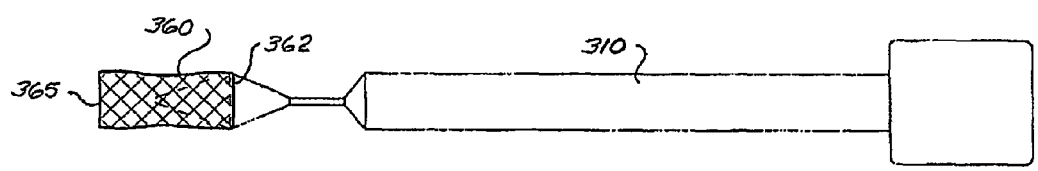
FIG. 26

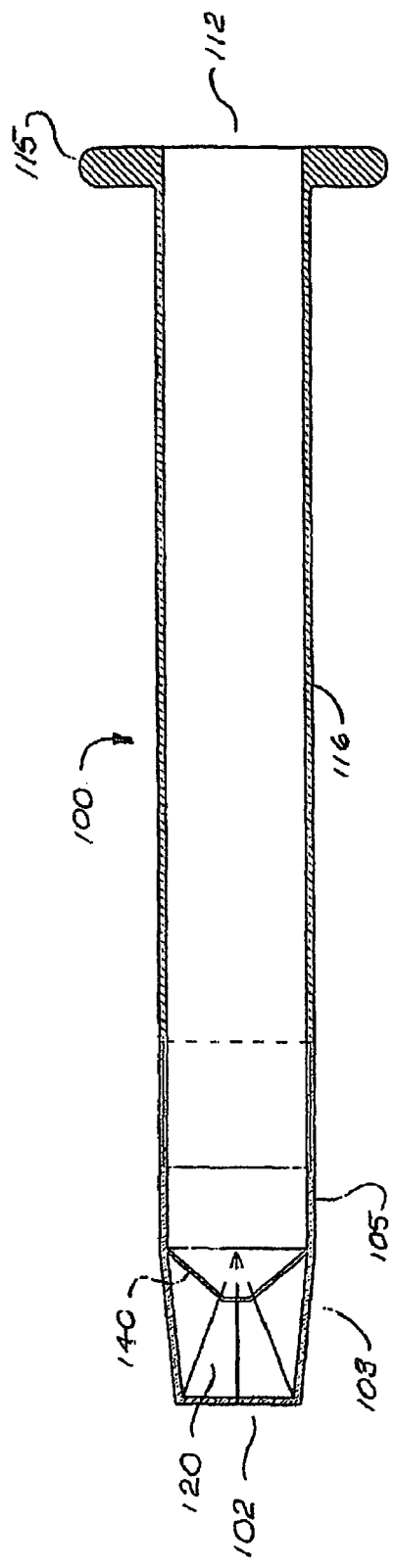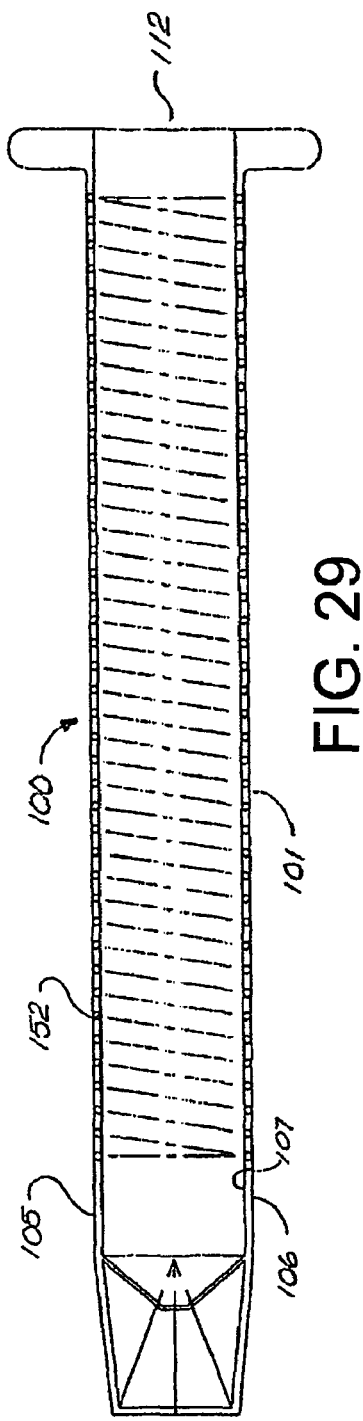

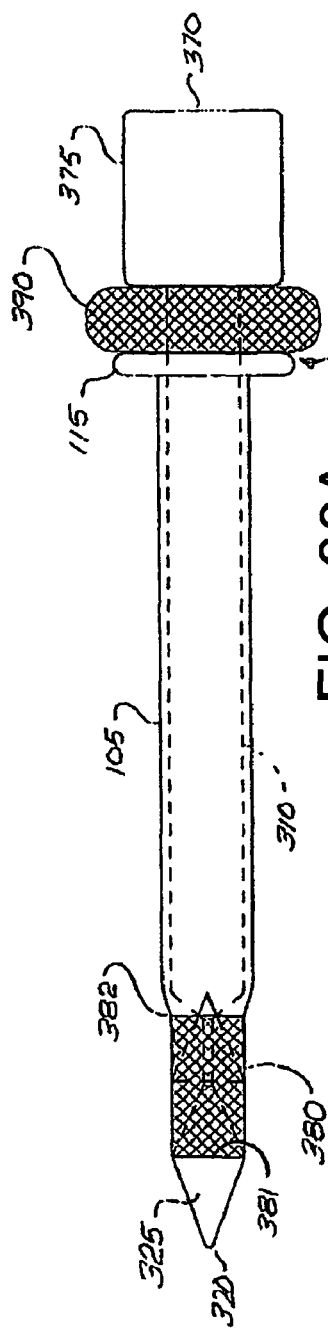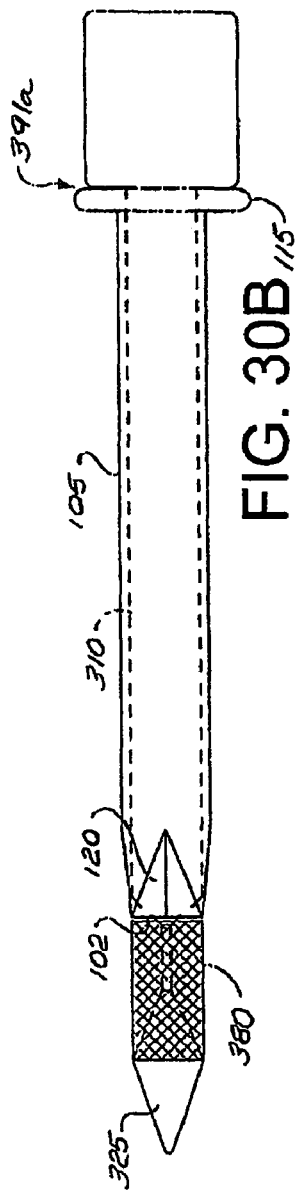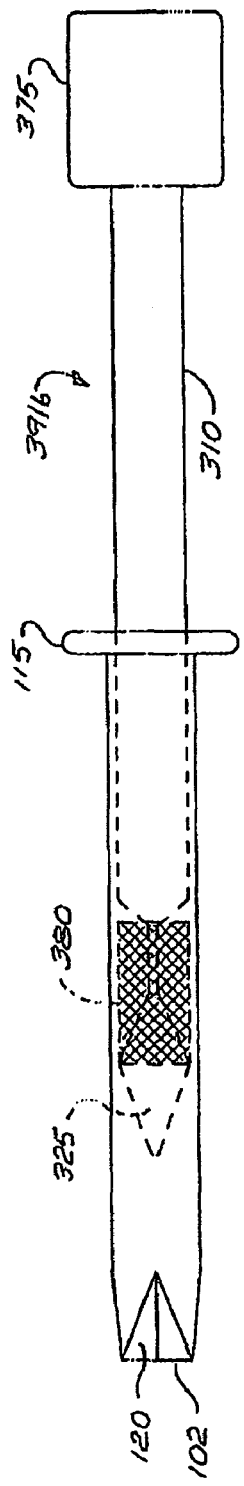

SELF-SEALING CANNULA HAVING INTEGRATED SEALS

BACKGROUND OF THE INVENTION

1. Field of the Invention

This invention generally relates to surgical access devices and, in particular, to a self-sealing cannula having integrated seals.

2. Discussion of the Relevant Art

Access devices used in laparoscopic surgery generally include a cannula providing an operative channel that traverses a body wall and extends into an associated body cavity. The cannula is generally equipped with a proximal seal housing that remains external to the body cavity. The seal housing generally contains a combination of seal members sized and configured to maintain an elevated pressure within the body cavity.

The most common seal construction within the seal housing comprises a first seal sized and configured to maintain a pressure differential when an instrument or tool is within the cannula and seal housing. This type of seal is commonly known as a septum seal. A typical septum seal is an elastomeric sheet or form with a hole or piercing generally at the center. A septum seal is generally dedicated to a range of instruments or tools, such as from five millimeters to twelve millimeters. To complete the seal system of a typical cannula seal-housing, a zero seal or zero seal is normally employed. Zero seals or zero seals are generally configured to be either open or closed and often rely on gradient pressure to form a complete seal. Examples of such zero seals or zero seals may include flap-valves, ball-zero seals and duckbill valves. The septum seal is preferably located proximal of the second seal so that an instrument or tool blocks the orifice in the septum before breaching the second seal or zero seal.

The cannulas and seal housings are generally constructed of rigid materials. The most common material is plastic for disposable devices and metal for reusable devices. The seal housing extends for a distance proximally and is generally quite wider in diameter than the cannula. A typical cannula is approximately 100 mm long and a typical seal housing is 20-50 mm in length. The diameter of a typical cannula will accommodate instruments in the range of five millimeters to twelve millimeters. The diameter of the respective seal housings may range from twenty millimeters for a five-millimeter cannula to thirty millimeters for a twelve-millimeter cannula.

Disadvantages of large seal housings include higher weight, cost and the limitation they place on the full use of surgical instruments passing through the seal housings. For instance, a surgical instrument having an overall shaft length of fifteen inches may have a reduced working length of about thirteen inches when placed through the seal housing of the prior art. That is, the working length is reduced by at least two inches. Moreover, there is the cost of complex seal housings to consider. In particular, they generally comprise a plurality of molded plastic components that address the complex nature of laparoscopic access devices. Accordingly, there is a need in the art for a surgical access device having integrated seals that does not require an external seal housing.

SUMMARY OF THE INVENTION

The present invention relates to a surgical access device comprising an elongate tubular member having a working channel and an axis extending between a proximal end and a distal end, a septum seal integrally formed at the distal end of the tubular member, and a zero seal or zero seal disposed at the distal end of the tubular member and distal to the septum seal, the zero seal being sized and configured to seal when no instrument is in place within the working channel of the tubular member, and the zero seal being coupled to the septum seal and having properties to float with the septum seal relative to the tubular member. The tubular member may be formed from an elastomeric material. The tubular member has a wall that may be rigid or semi-rigid. The tubular member may be reinforced with a coil along a portion of the tubular member. The tubular member may include a distal, mechanically deployable shielding portion. The zero seal may be a duckbill seal constructed with one or more intersecting sealing portions. The surgical access device may further comprise a retaining portion such as a flange or a ring at the proximal end of the tubular member. In one aspect of the invention, the tubular member and the septum seal are molded together as a single unit and the zero seal is bonded or fused to the septum seal.

In another aspect, the tubular member, the septum seal and the zero seal are all molded together or integrally formed as a single unit. The tubular member may further comprise flexibility enhancing features to allow the tubular member to flex in response to a motion of a surgical instrument within the working channel of the tubular member. The flexibility enhancing features may be formed around the distal end of the tubular member or all along the tubular member. It is appreciated that the flexibility enhancing features provide a floating motion to the septum seal and the zero seal.

The surgical access device may further comprise a second septum seal disposed at or near the proximal end of the tubular member. In this aspect of the invention, the second septum seal provides leak protection in the event that the septum seal is over-stressed or damaged. With this aspect of the invention, the surgical access device may further comprise a second zero seal disposed at or near the proximal end of the tubular member distal to the second septum seal.

In another aspect of the invention, the tubular member may have at least one section that gradually tapers to facilitate placement of the access device through a body wall. The tubular member may also include at least one region having a reduced wall section or thickness. The reduced thickness region may be at or near the distal end of the tubular member.

In yet another aspect of the invention, the surgical access device may further comprise a placement device for placing the access device. The placement device may be an obturator operable to pierce or penetrate tissue. The placement device of the invention includes an elongate shaft having a proximal end, a mid-portion and a distal end. In one aspect, the proximal end includes a handle sized and configured to be held by a user, the mid-portion has a reduced profile that is sized and configured to extend through the tubular member of the access device, and the distal end that is shaped like an hourglass. The distal end may comprise a tapered, cone-shaped member. The shaft may further comprise a venting lumen to provide fluid communication between the distal end and the proximal end of the placement device. The placement device may further comprise an elastomeric shield member sized and configured to fit over the shaft such that when the placement device is withdrawn, the elastomeric shield member everts and is drawn into distal openings of the septum seal and the zero seal.

The duckbill seal of the zero seal may comprise of opposing lip portions separated by a slit portion. In this aspect, the opposing lip portions are coated with or attached to a soft or occlusive material. The occlusive material is one of KRATON®, polyurethane or the like. It is appreciated that the occlusive lip portions allow a surgical item such as a suture to extend through the slit portion without disrupting the seal.

In another aspect of the invention, a method of placing a surgical access device across a body wall and into a body cavity is disclosed, the method comprising the steps of: providing the surgical access device having an elongate tubular member including a working channel and an axis extending between a proximal end and a distal end, a septum seal disposed at the distal end of the tubular member, and a zero seal disposed at the distal end of the tubular member distal to the septum seal, the zero seal being coupled to the septum seal and having properties for floating with the septum seal relative to the tubular member; providing a placement device comprising an elongate shaft having a proximal end, a mid-portion and a distal end; inserting the placement device into the working channel of the tubular member with the distal end of the placement device extending beyond the distal end of the tubular member; and advancing the placement device and the tubular member through the body wall and into the body cavity. The method of placing the access device may further comprise the step of removing the placement device from the tubular member to open the working channel into the cavity. The method of placing the access device may further comprise the step of inserting a surgical instrument into the working channel of the tubular member to perform surgery within the cavity.

In yet another aspect of the invention, a method of forming a one-piece surgical access device is disclosed, the access device having an elongate tubular member including a working channel and an axis extending between a proximal end and a distal end, a septum seal disposed at the distal end of the tubular member, and a zero seal disposed at the distal end of the tubular member distal to the septum seal, the zero seal being coupled to the septum seal and having properties for floating with the septum seal relative to the tubular member, the method comprising the steps of: placing the tubular member pre-form in a compression mold cavity having a proximal end and a distal end; placing the septum seal pre-form in the distal end of the compression mold cavity; and compressing the tubular member pre-form and the septum seal pre-form so as to mold said pre-forms into a preferred condition.

In yet another aspect of the invention, a method of forming a zero seal of a surgical access device is disclosed, the access device having an elongate tubular member including a working channel and an axis extending between a proximal end and a distal end, a septum seal disposed at the distal end of the tubular member, and the zero seal disposed at the distal end of the tubular member distal to the septum seal, the zero seal being coupled to the septum seal and having properties for floating with the septum seal relative to the tubular member, the method comprising the steps of: inserting slit-forming members into a mold core of the zero seal having lateral extremities; and sharpening the slit-forming members at the lateral extremities. The method of forming the zero seal of the surgical access device may further comprise the step of tapering the slit-forming members at the lateral extremities to form an undercut slit or slit end portion. The method of forming the zero seal of the surgical access device may further comprise the step of removing the core and slitting the terminal, lateral portion of the molded slit as the core is being removed.

These and other features and advantages of the invention will become more apparent with a discussion of preferred embodiments in reference to the associated drawings.

DESCRIPTION OF THE DRAWINGS

FIG. 5 is a detail side view of the self-sealing laparoscopic cannula of the invention;

FIG. 6 is a section side view of the self-sealing laparoscopic cannula of the invention with no surgical instrument in place;

FIG. 7 is a section side view of the self-sealing laparoscopic cannula of the invention with a large surgical instrument in place;

FIG. 8 is a section side view of the self-sealing laparoscopic cannula of the invention with a small surgical instrument in place;

FIG. 14 is a side section view of a self-sealing laparoscopic cannula in accordance with another embodiment of the invention having a distally located seal system and a redundant proximal septum seal;

FIG. 15 is a side section view of a self-sealing laparoscopic cannula in accordance with another embodiment of the invention having a distally located seal system and a redundant proximal zero seal;

FIG. 23 is a side view of a placement tool of the invention for use in a first condition;

FIG. 24 is a side view of a placement tool of the invention for use in a second condition;

FIG. 25 is a side view of a placement tool of the invention for use in a third condition;

FIG. 26 is a side view of a placement tool of the invention for use in a fourth condition;

FIG. 28 illustrates a self-sealing laparoscopic cannula in accordance with another embodiment of the invention having a rigid cannula;

FIG. 29 illustrates a self-sealing laparoscopic cannula in accordance with another embodiment of the invention having a reinforced elastomeric cannula;

FIGS. 30(A)-30(C) illustrate a placement device for use in placing a laparoscopic cannula in accordance with another embodiment of the invention having a rigid and movable shield;

DESCRIPTION OF PREFERRED EMBODIMENTS AND BEST MODE OF THE INVENTION

Figure 1:
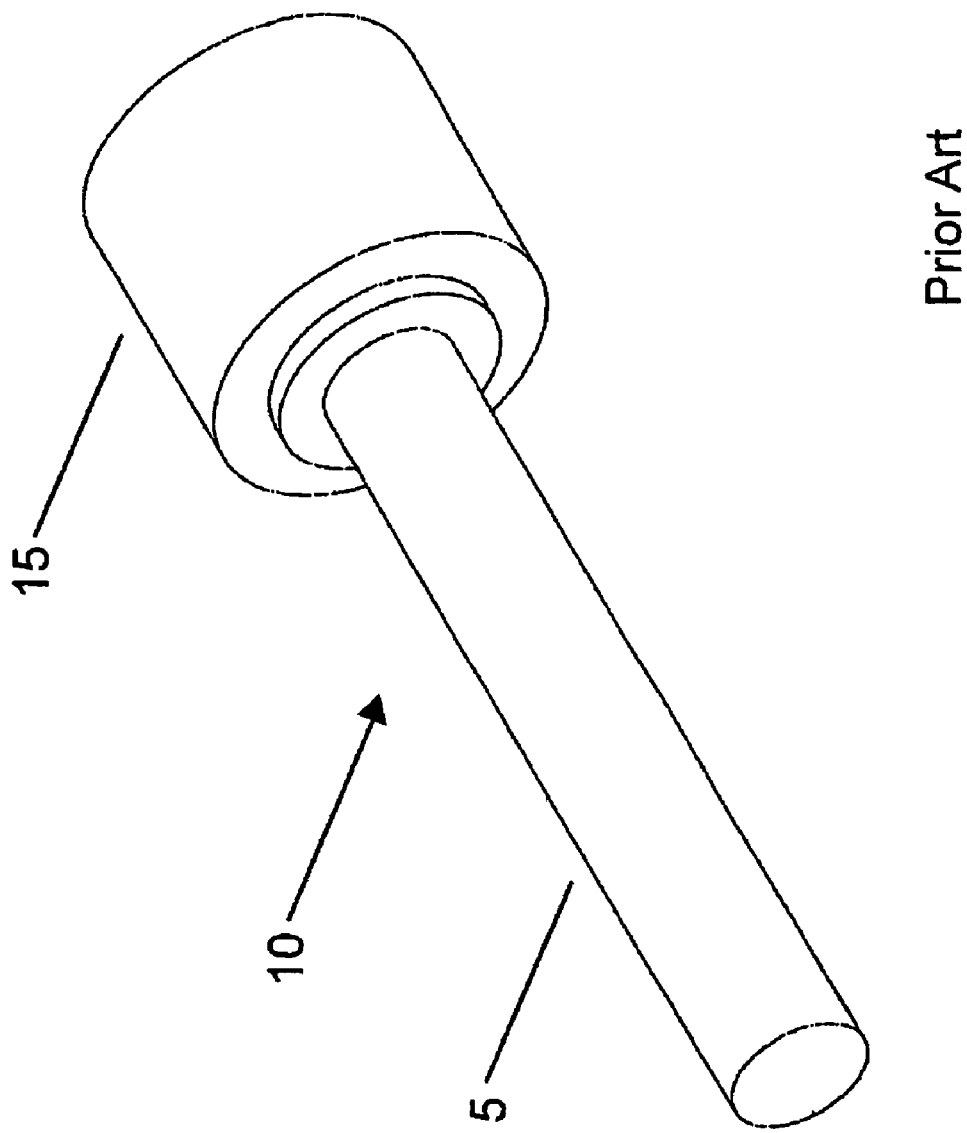
FIG. 1 is a perspective view of a laparoscopic cannula and seal housing according to the prior art.
Figure 2:
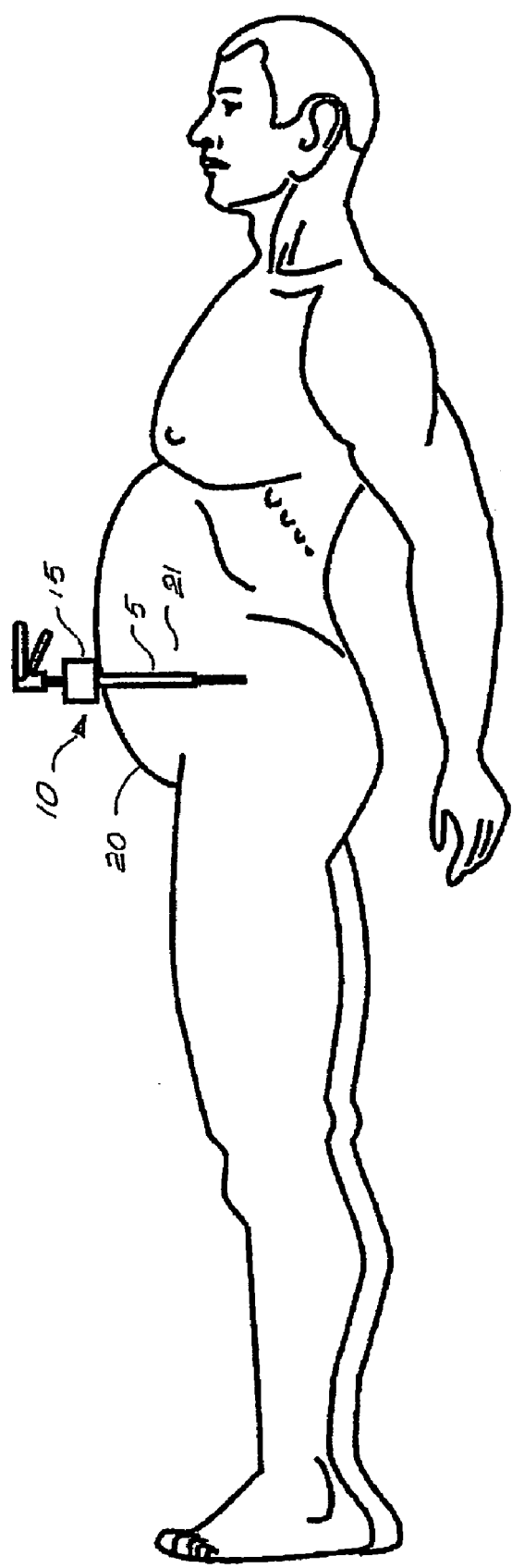
FIG. 2 is a side view of a typical laparoscopic surgical procedure.

Referring to FIG. 1, there is shown a laparoscopic surgical access device 10 of the prior art comprising a cannula 5 and a seal housing 15. Cannula 5 is sized and configured to pass through a body wall and into a body cavity. The seal housing is sized and configured to contain a seal combination that isolates the internal body cavity from the external environment. Positive pressure is provided to the internal body cavity so that the body wall is distended. FIG. 2 illustrates a common laparoscopic surgical procedure where access device 10 of the prior art has been placed through a body wall 20 and into a body cavity 21. It is clearly seen that the seal housing 15 of the prior art extends for an appreciable distance externally.

Figure 3:
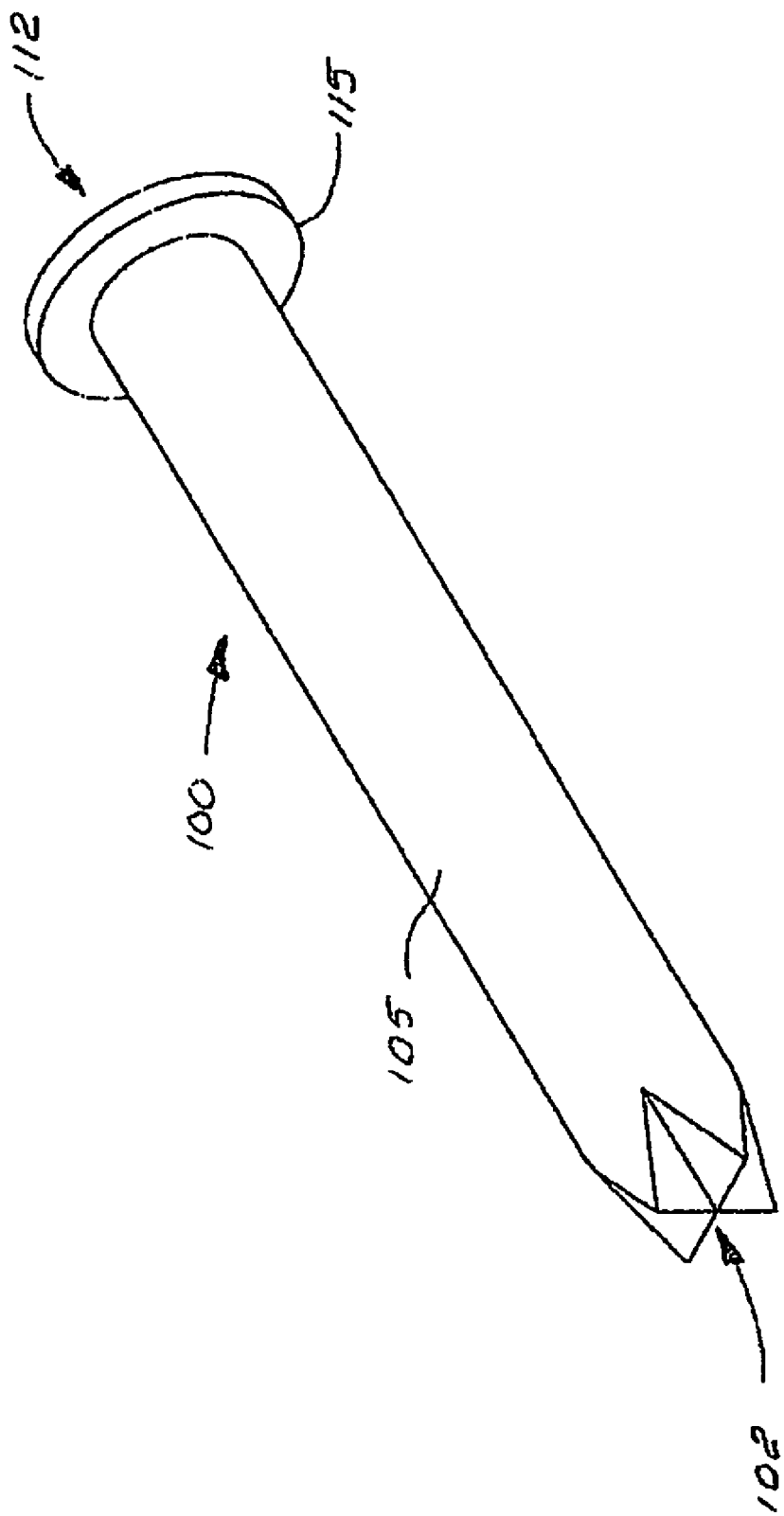
FIG. 3 is a perspective view of a self-sealing laparoscopic cannula according to the invention.

Referring to FIG. 3, there is shown an access device 100 of the present invention having a generally elongate, tubular body 105, a proximal end 112 and a distal end 102. The elongate, tubular body 105 comprises an elastomeric cannula that is sized and configured to pass through a body wall 20 and into a body cavity 21. The proximal end 112 of the elongate, tubular body 105 may be open and may be constructed with an enlarged portion or flange ring 115. The distal end 102 of the elongate, tubular body 105 comprises a septum seal and a check valve or zero seal.

Figure 4:
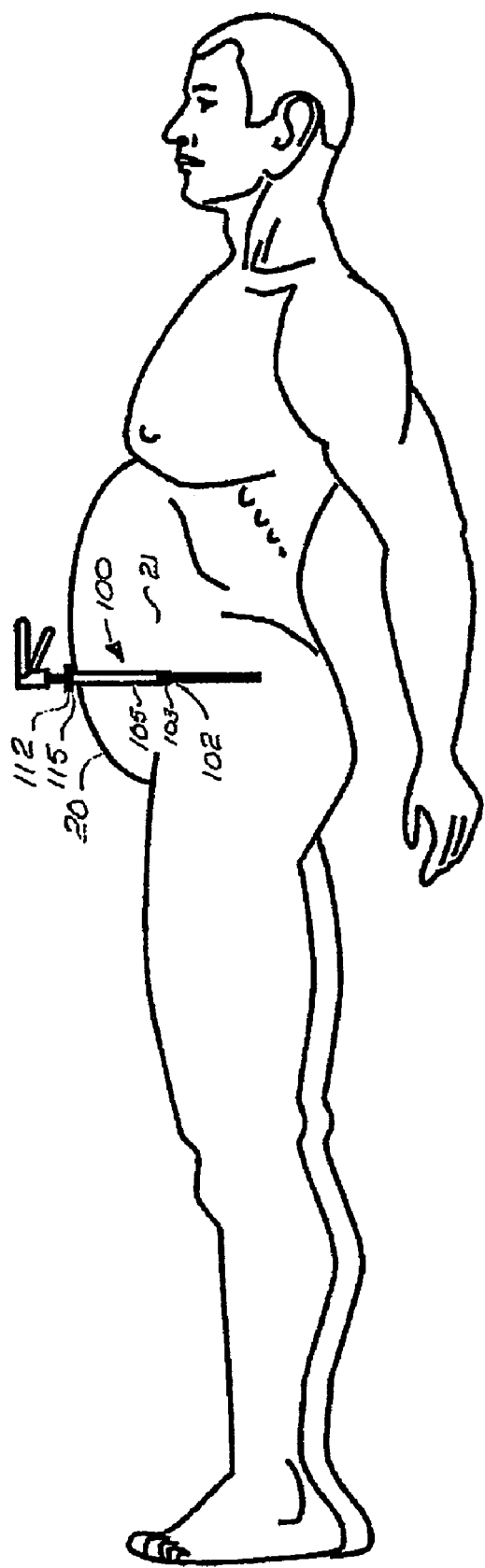
FIG. 4 is a side view of a laparoscopic surgical procedure employing the invention.

Referring to FIG. 4, the access device 100 of the invention is seen in a laparoscopic surgical procedure where the elongate, tubular body 105 or cannula is placed through the body wall 20 and into the body cavity 21. The proximal end 112 of the elongate, tubular body 105 remains external to the body wall 20 and may be restricted from further entry into the body cavity 21 by the enlarged proximal flange or ring 115. The distal end 102 of the elongate, tubular body 105 further includes a seal system 103 comprising a check valve or zero seal within the body cavity 21 and serves to isolate the body cavity 21 from the external environment. The distal seal system 103 of the invention allows the body cavity 21 to be pressurized.

With reference to FIGS. 5 and 6, an embodiment of the present invention is shown comprising a tubular, elongate body 105 having an outer surface 106 and an inner surface 107. The wall section is preferably thin and flexible. A first seal 140 and a second seal 120 of the seal system 103 are placed at the distal end 102 of the elongate, tubular body 105. In this embodiment, the first seal 140 is a septum seal that is molded or formed as the elongate, tubular body 105 is molded or formed so that the first seal 140 and the elongate, tubular body 105 are a single piece. As illustrated in FIG. 6, the septum seal can have a frusto-conical shape extending from the inner surface 107 of the tubular body 105 radially inward to an orifice 145 of the septum seal. A bonding feature 141 may be provided for attaching the first seal 140 to the second seal 120. The second seal 120 may comprise a duckbill seal that is constructed with two intersecting sealing portions. This construction is commonly referred to as a double duckbill seal. The zero seal is positioned at the distalmost extent of the surgical access device 100 and operates to provide backflow prevention into a channel 122 (FIGS. 7, 8), when no instrument is in place within the channel 122. The double duckbill construction is particularly useful in the invention because there are a plurality of folds formed in the outer surface 106 of the tubular body 105 at the distal end 102 along several lines 121 with each fold of the plurality of folds extending proximally from the distalmost extent of the access device 100, and it is easily inserted through the body wall 20. In the present embodiment, the elongate, tubular body 105, a proximal retaining portion 115, the distal first seal 140 and the distal second seal 120 are all molded or formed in a monolithic or one-piece construction.

Referring to FIGS. 7 and 8, the access device 100 of the present invention is shown with laparoscopic surgical instruments 200, 250 in place within a lumen or channel 122 of the access device 100. A large instrument 200, one having a large diameter nearly that of the inside diameter of the access device 100 itself, substantially fills the lumen 122 and substantially deforms the first seal 140 and second seal 120 as shown in FIG. 7. A small instrument 250, one having a diameter substantially less than the inside diameter of the access device 100 itself, slightly deforms the first seal 140 and the second seal 120 as shown in FIG. 8. Thus, an orifice 145 (FIG. 6) of the first seal 140 or septum seal is sized with a diameter that is substantially smaller than an inside diameter of the elongate tubular body 105 of the access device 100.

Figure 10:
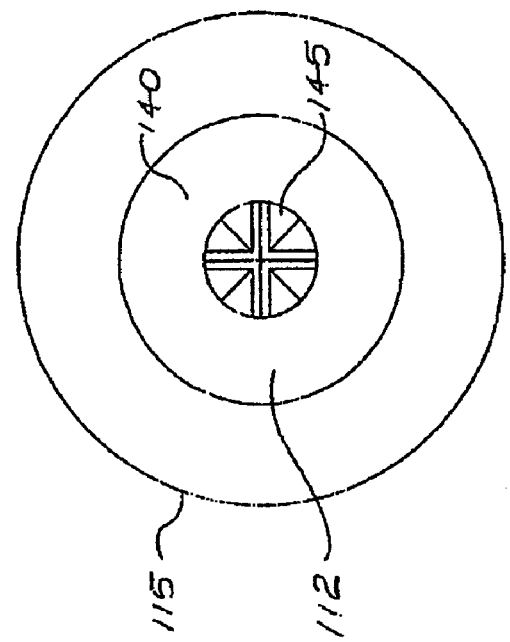
FIG. 10 is a proximal end view of the self-sealing laparoscopic cannula of the invention.
Figure 9:
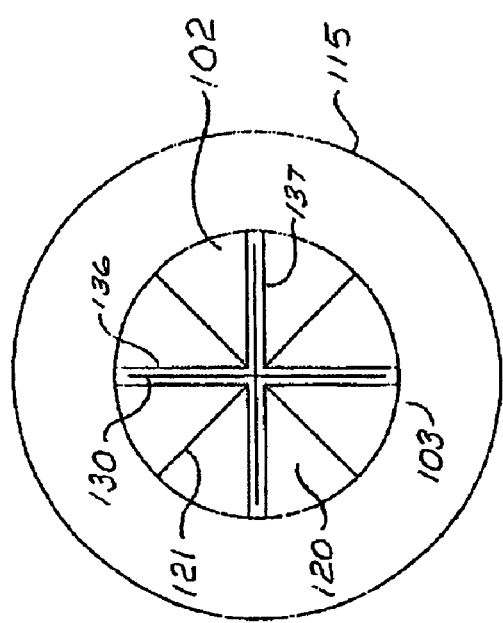
FIG. 9 is a distal end view of the self-sealing laparoscopic cannula of the invention.

Referring now to FIGS. 9 and 10, one appreciates the distal end 102 of the access device 100 as comprising a second seal 120 having a check valve or zero seal formed as an intersection of two occlusive portions 136, 137 of a double duckbill. The proximal end view of FIG. 10 reveals that the first seal 140 is placed proximal of the second seal 120. The first seal 140 comprises a septum having an orifice 145 that is sized and configured to seal in conjunction with a specific range of usable instruments.

Figure 11:
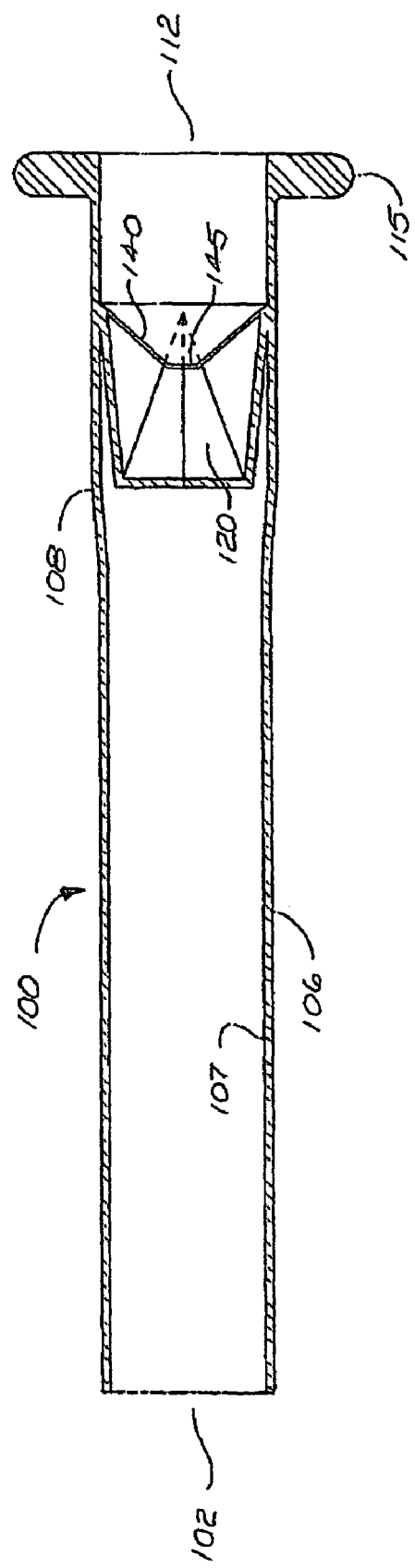
FIG. 11 is a section side view of a self-sealing laparoscopic cannula in accordance with another embodiment of the invention having a proximally located seal system.

Referring to FIG. 11, there is shown a section side view of a self-sealing laparoscopic cannula in accordance with another embodiment of the invention having a proximally located seal system. In particular, FIG. 11 illustrates a self-sealing laparoscopic cannula where a first seal 140 and a second seal 120 are molded as part of the elongate, tubular body 105. In this embodiment, the first seal 140 and the second seal 120 may be molded with, or attached near to, the proximal end 112 of the elongate, tubular body 105. Alternately, the seal members 140, 120 may be attached as a second operation by bonding or fusing to form the attachment. An enlargement 108 may be provided to allow deformed seals 140, 120 material to move away from an instrument within the access device 100.

Figure 12:
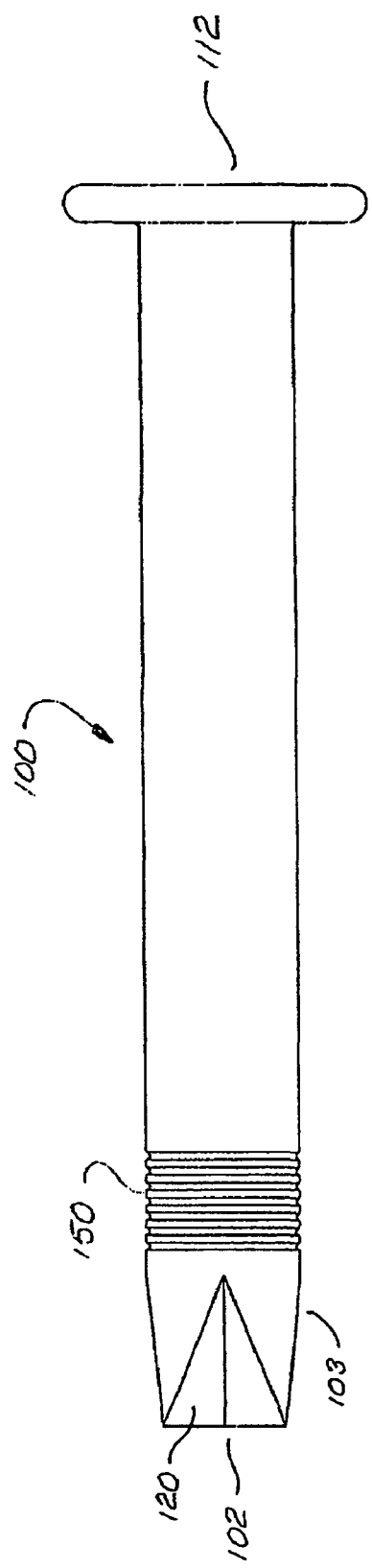
FIG. 12 is a perspective view of a self-sealing laparoscopic cannula in accordance with another embodiment of the invention having a convoluted distal portion.
Figure 13:
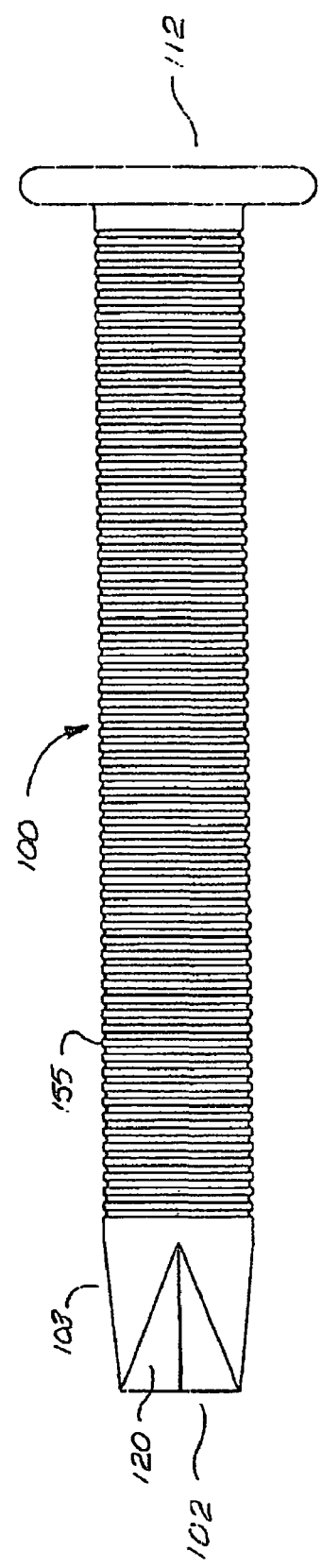
FIG. 13 is a perspective view of a self-sealing laparoscopic cannula in accordance with another embodiment of the invention having a convoluted tubular cannula.

Referring to FIGS. 12 and 13, there are shown perspective views of self-sealing laparoscopic cannulas in accordance with additional embodiments of the invention having a convoluted distal portion and a convoluted tubular cannula, respectively. Specifically, further embodiments of the invention are shown having a plurality of flexibility enhancing features 150 arranged upon the elongate, tubular body 105. As illustrated in FIG. 12, the flexibility enhancing features 150 allow the distal seal portion 103 of the elongate, tubular body 105 to flex in response to a motion of an instrument within the working channel or lumen of the elongate, tubular body 105. As an instrument is moved within the working channel, the distal end 102 moves appropriately without distorting the sensitive orifice 145 associated with the first seal 140. The motion associated with this configuration is referred to as "floating". In this instance, the first and second seals 140, 120 associated with the distal end 102 of the elongate, tubular body 105 constitute "floating seals".

Referring to FIG. 13, a further embodiment contemplates an elongate, tubular body 105 having flexibility enhancing features 155 arranged along the entire length of the body 105. This results in an elongate body 105 that may be further elongated by stretching so that the diameter is reduced to facilitate introduction into the body cavity 21 through the body wall 20.

Figure 16:
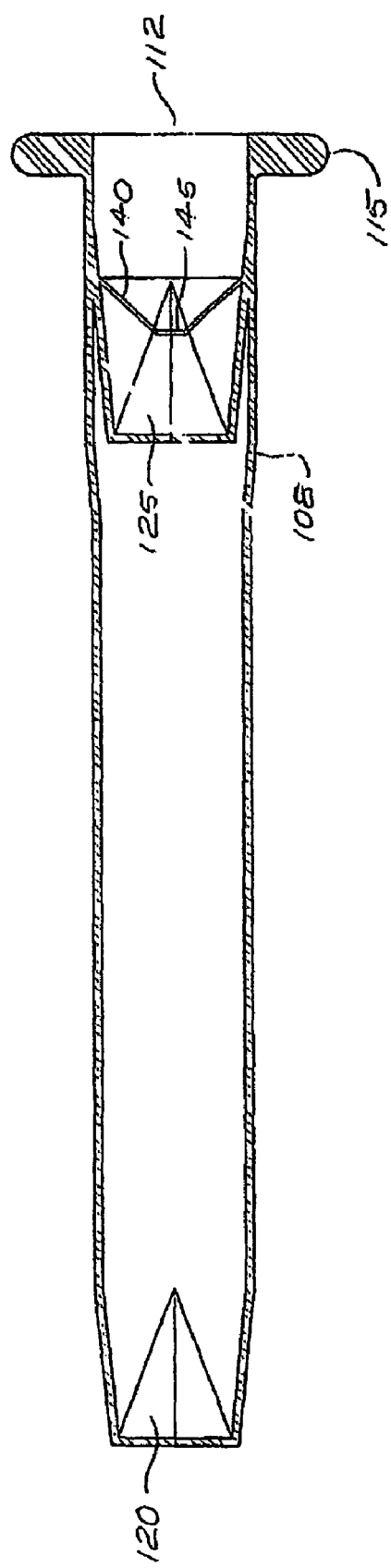
FIG. 16 is a side section view of a self-sealing laparoscopic cannula in accordance with another embodiment of the invention having a distally located first seal and a redundant proximal septum seal and a redundant zero seal.

Referring now to FIGS. 14, 15 and 16, the elongate, tubular body 105 is shown having a first seal 140 formed at the distal end 102. A second seal 120 is then attached over the first seal 140 to form a seal system 103 that is fluid tight between the exterior of the tubular body 105 and the interior 122 of the tubular body 105. The interior 122 of the tubular body 105 provides a working channel for the passage of surgical instruments into a pressurized body cavity 21. The first seal 140 is sized and configured to provide a fluid tight arrangement when an instrument is in place within the working channel 122. The second seal 120 is sized and configured to seal when no instrument is in place within the working channel 122. The first and second seals 140, 120 cooperate to provide a unique arrangement where there are strict requirements regarding friction, drag and durability. An alternate embodiment as shown in FIG. 14 contemplates the use of an additional first seal 140 at or near the proximal end 112 of the elongate, tubular body 105. The additional, proximal first seal 140 provides leak protection in the event that the primary first seal 140 is over-stressed or is damaged.

With reference to FIG. 15, the elongate, tubular body 105 and integral, distal first seal 140 are shown. This embodiment further contemplates the placement of the second seal 120 at or near the proximal end 112 of the elongate, tubular body 112. Additionally, there is an enlargement 108 in the diameter of the elongate, tubular body 105 to accommodate displaced seal material 120 in the presence of a large instrument within the working channel 122 of the access device 100.

Referring to FIG. 16, the elongate, tubular body 105 and integral, distal second seal 120 are shown. This embodiment further contemplates the placement of a redundant second seal 120 at or near the proximal end 112 of the elongate, tubular body 105. Additionally, a first seal 140 is placed at or near the proximal end 112 of the elongate, tubular body 105. In this arrangement, an instrument placed into the working channel 122 of the invention is first sealed against the proximal, first seal 140. Next, the instrument breaches the proximally located, redundant, second seal 120. Finally, the instrument breaches the distally placed, second seal 120.

Figure 17:
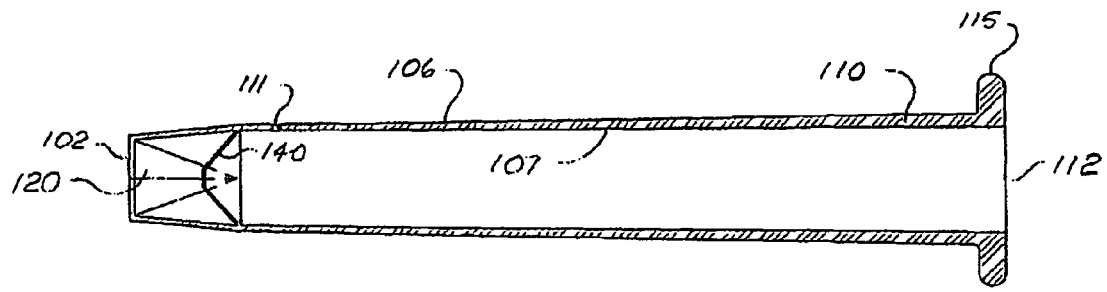
FIG. 17 is a side section view of a self-sealing laparoscopic cannula in accordance with another embodiment of the invention having a tapered tubular body.

Referring to FIG. 17, the elongate, tubular body 105 is shown having a generally graduated or tapered wall sections 110, 111. The tapered wall provides a greater degree of flexibility in the region of the thin wall 111 than in the region of the thick wall 110. The gradual taper also facilitates placement of the access device 100 through a body wall 20.

Figure 18:
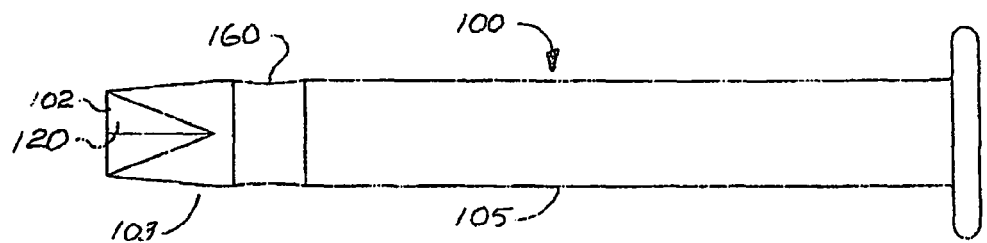
FIG. 18 is perspective view of a self-sealing laparoscopic cannula in accordance with another embodiment of the invention having a more flexible distal portion.
Figure 19:
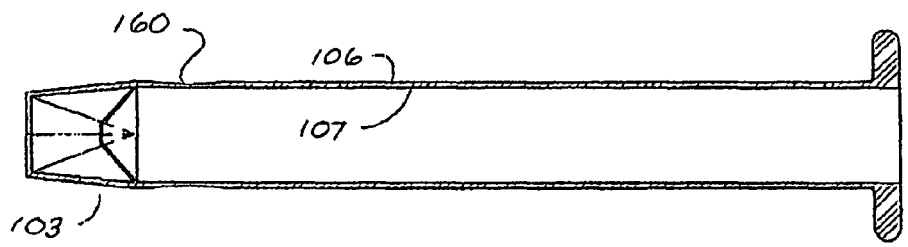
FIG. 19 is a side section view of a self-sealing laparoscopic cannula in accordance with another embodiment of the invention having a more flexible distal portion.

It may be seen from FIGS. 18 and 19 that the elongate, tubular body 105 may additionally comprise a region that has a reduced wall section or thickness 160. The reduced thickness region 160 is preferably located at or near the distal end 102 of the elongate, tubular body 105. This configuration permits the seal system 103 to "float" in response to the motion of an instrument within the operative working channel 122 of the access device 100.

Figure 20A:
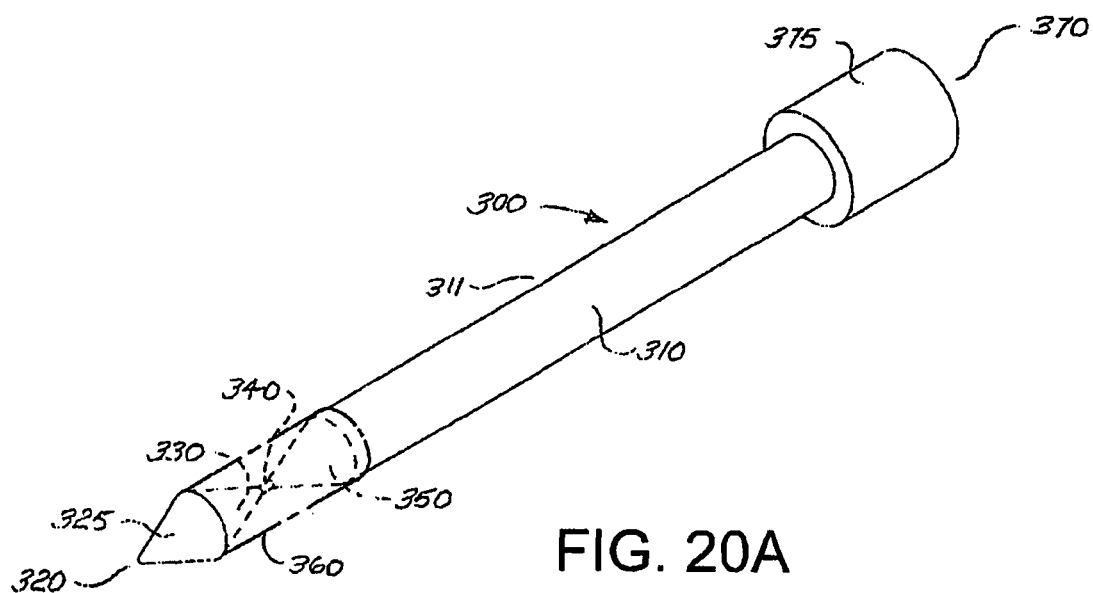
FIGS. 20(A) and 20(B) illustrate perspective views of a placement tool for use in placing a self-sealing laparoscopic cannula of the invention.
Figure 20B:
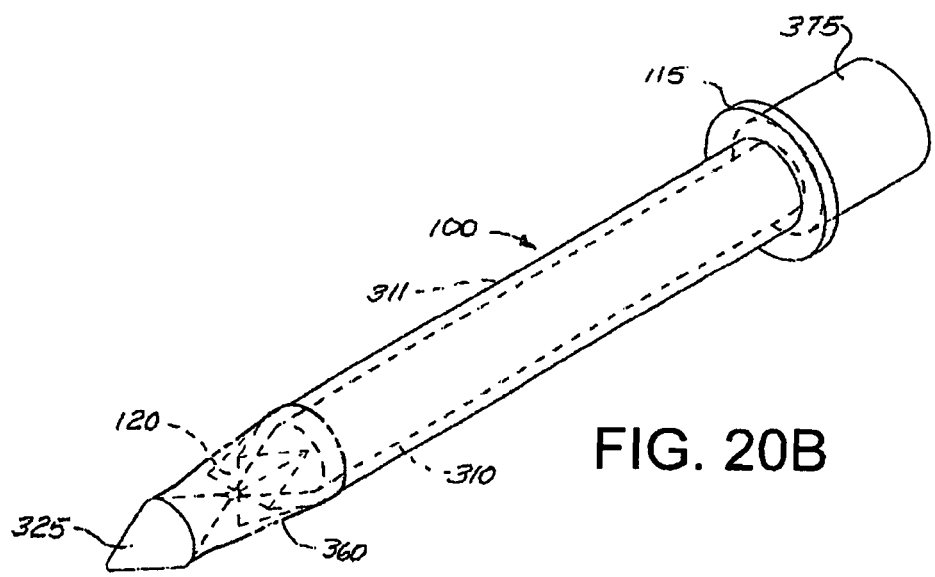

With reference to FIGS. 20(A) and 20(B), a device 300 for use in the placement of the elongate, tubular body 105 and seal system 103 is shown. The device 300 comprises an elongate shaft 310 having a proximal end 370, a mid-portion 311 and a distal end 320. The proximal end 370 is sized and configured to be held by a user and preferably comprises a handle 375. The mid-portion 311 is sized and configured to extend through the elongate, tubular body 105 and extend there-through. The distal end portion 325 of the placement device 300 is sized and configured to separate or penetrate the tissue of a body wall 20 and facilitate the passage of the tubular body 105 and seal system 103 there-through.

Figure 21:
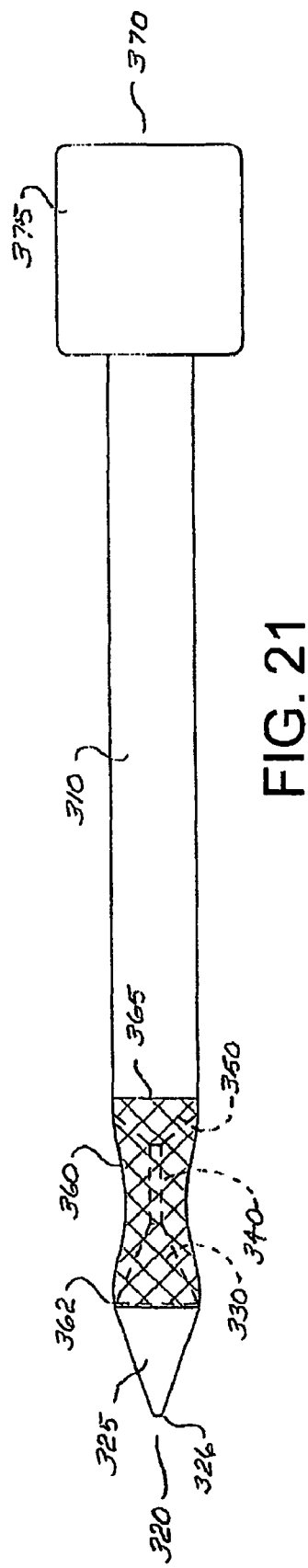
FIG. 21 is a side view of another embodiment of a placement tool for use in placing a self-sealing laparoscopic cannula of the invention.
Figure 22:
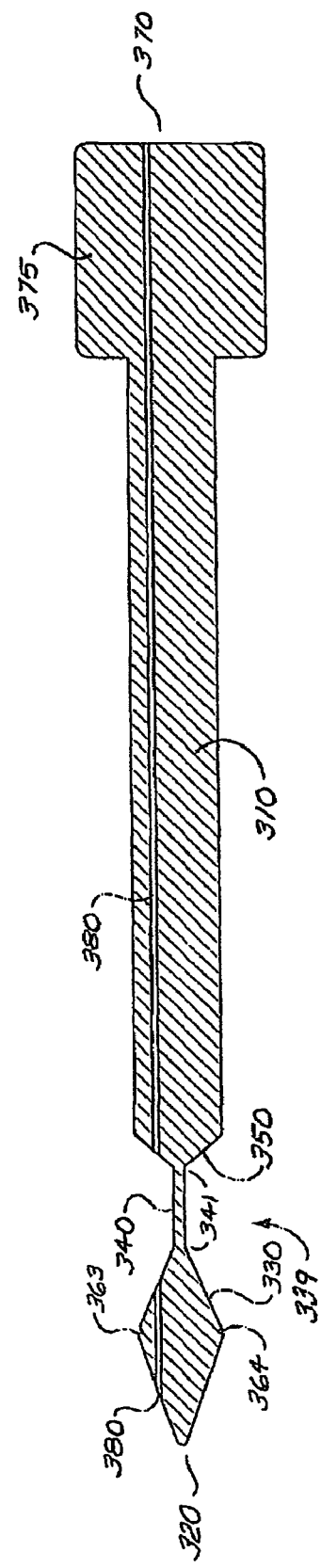
FIG. 22 is a side section view of yet another embodiment of a placement tool for use in placing a self-sealing laparoscopic cannula of the invention.

FIGS. 21 and 22 illustrate side views of the placement device or obturator 300 for use in the placement of the elongate, tubular body 105 and seal system 103 of the invention. In particular, FIG. 21 illustrates the distal end 320 of placement device 300 having a first, conically tapered member 325 that begins with a point 326 and extends for a distance to a diameter approximately that of the inside diameter 107 of the elongate, tubular body 105 of the access device 100. Extending proximally from the largest diameter 363 of the distal first, conical portion 325, there is a second conical, continuing portion 330 that reduces a portion of the diameter of the placement device 300 to a preferred small diameter 340 for a distance 341 extending proximally. The small diameter 340 is sized and configured to pass through the seal system 103 of the invention without deforming the seal material to an unacceptable point while the placement device 300 is within the access device 100. The reduced diameter portion 340 extends for a distance 341 and subsequently begins to increase in diameter conically 350 to the full diameter of the elongate shaft 310. In a preferred embodiment, this third conical portion 350 matches the angle of the first seal member 140. In addition, a venting lumen 380 is provided within the shaft 310 of the placement device 300 providing fluid communication between the distal end 320 of the placement device and the proximal end 370 of the placement device 300.

The distal, reduced diameter portion 339 of the placement device 300 resembles an hourglass. In a preferred embodiment, there is a retention feature 364 associated with the large diameter portion 363 of the distal portion 325 of the placement device 300. An elastomeric shield 360 is associated with the retention feature 364 and extends proximally from a first end 362 to a second end 365 for a distance sized and configured to cover the reduced diameter portion 339 of the placement device 300. The elastomeric shield 360 is sized and configured to fit tightly over the elongate shaft 310 of the placement device 300 for a short distance to prevent features of the second seal 120 from intercepting body wall 20 tissue as the access device 100 is urged through the body wall 20 and into the body cavity 21. The elongate, tubular body 105 and seal system 103 are placed over the placement device 300 of the invention so that the distal second seal 140 is at rest over the reduced diameter portion of the placement device. The elastomeric shield is stretched over the distal end 120 of the elongate, tubular body 105. The elastomeric shield 360 thus forms a smooth transition between the various components of the invention. Once proper placement of the access device 100 is confirmed, the placement device 300 may be withdrawn from the elongate, tubular body 105. The elastomeric sleeve 360 everts and follows the placement device 300 as it is withdrawn from the tubular body 105.

Referring to FIGS. 23-26, the assembly of the invention is shown in the steps of placement. In a first condition as illustrated in FIG. 23, the placement device 300 is shown within the access tube 105 in a stored and ready for use condition. This first condition illustrates the smooth transitions between the distal end 320 of the placement device and the distal seal system 103 of the access device 100. Upon confirmed placement of the access device 100, the placement device 300 may be withdrawn from the access device 100. As the placement device 300 is withdrawn, the elastomeric shield member 360 everts and is drawn into the distal openings of the distal seal members 140, 120 of the access device 100. Once the placement device 300 is fully withdrawn, it can be seen that the elastomeric shield member 360 is fully everted. The access device 100 is now ready for use.

Figure 27:
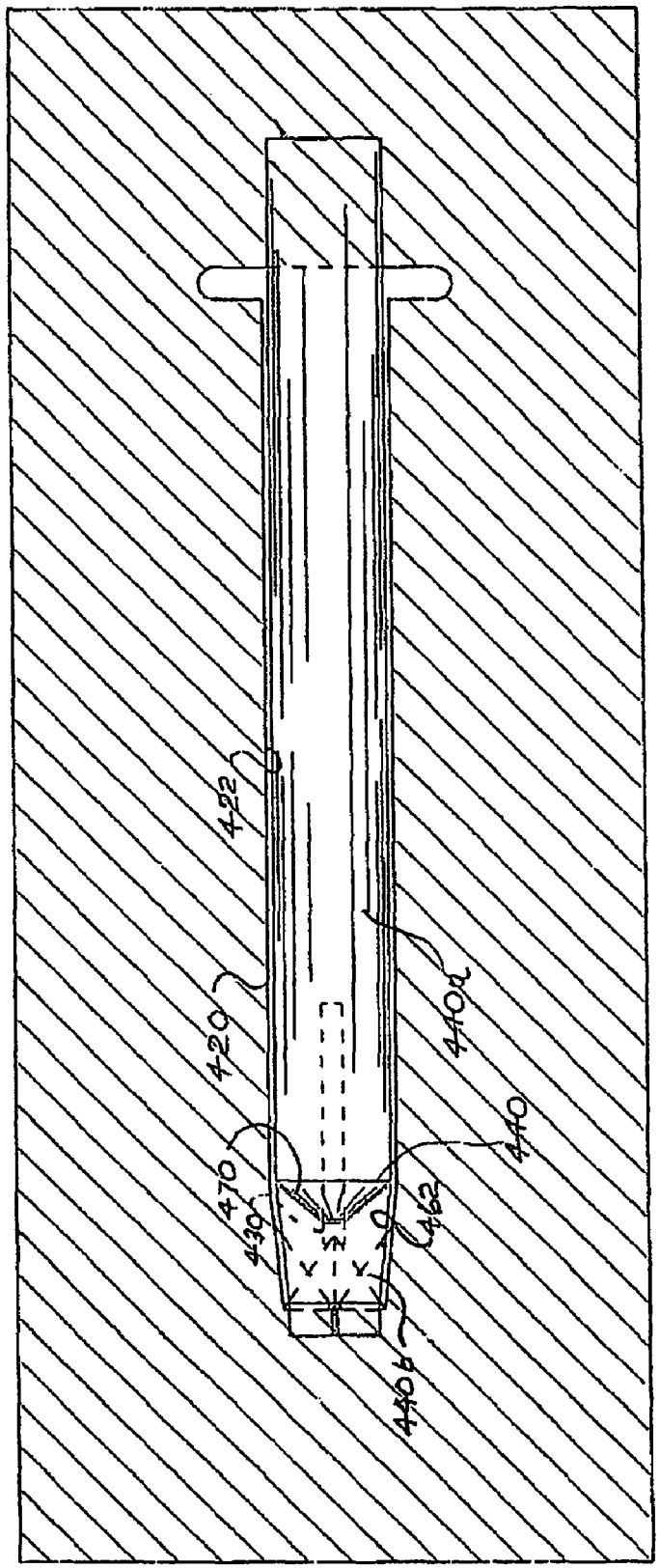
FIG. 27 illustrates another method for molding a self-sealing laparoscopic cannula of the invention.

With reference to FIG. 27, a method for molding the elastomeric cannula 105 and seal system 103 of the present invention is shown comprising a cavity 420 and a core 440. The core 440 may comprise one or more mating portions 440a, 440b that allow the first seal 140 and the second seal 120 to be integrally formed with the elongate, tubular body or cannula 105. The first core portion 440a forms the internal lumen 422 of the tubular body 105 and the distally facing surface 470 of the first seal or septum 140. A portion 430 of the first core 440a extends through the first seal or septum 140 and forms the orifice 145 there-through. A second portion 440b of the core 440 is removably attached to the extending portion 430 and forms the internal cavity 462 within the double duckbill seal or check valve 120. After an elastomeric material has flowed into the cavity 420 and around the first and second cores 440a, 440b, the first and second cores are disconnected so that the first core portion 440a may be removed proximally and the second core portion 440b may be removed distally through the intersecting slits in the distal end ribs of the double duckbill seal 120. In an alternate embodiment, the entire core 440 may comprise a one-piece construction that is removable proximally or distally from the elastomeric tubular body 105.

FIG. 28 illustrates the present invention alternately comprising a rigid or semi-rigid thin-walled cannula 116 and a distally placed seal system 103 according to the present invention. The first and second seals 140, 120, respectively, may be formed as a single unit and subsequently attached to the distal end of the cannula 116 or, alternately, may be formed separately so that the first seal 140 is attached to the cannula and the second seal 120 is attached to the first seal.

FIG. 29 illustrates an elastomeric cannula 101 that is reinforced so as to be substantially non-compressible radially. The reinforced cannula 101 may be preformed as a tube and subsequently placed into a compression or injection mold where the seal system 103 is formed at the distal end 102. A preferred embodiment contemplates the use of a metallic coil 152 as a reinforcement element along a portion of the elongate, tubular body 105 and terminating adjacent to the distal seal system 103. Alternately, a braided or woven reinforcement element 152 may be incorporated into the wall of the tubular body 105.

FIGS. 30(A)-30(C) illustrate an alternate placement device 300 comprising an elongate shaft 310 having a proximal end 370 and a distal end 320. The proximal end further comprises a handle 375. The shaft 310 of the placement device 300 is sized and configured to be axially movable within the working channel 122 of the access device 100. A rigid or semi-rigid shielding member 380 is associated with the distal portion 339 of the placement device 300 that is sized and configured to provide smooth transitions between the various elements of the access device 100 and associated seal system 103. The distal end 320 of the placement device 300 is sized and configured to penetrate tissue and provide entry into a body cavity. The distal portion comprises a tapered, cone-shaped member 325. The rigid or semi-rigid shield 380 extends proximally from the widest diameter portion 381 of the tapered, cone-shaped member 325 for a distance.

When the placement device is within the cannula 105 and seal system 103 of the invention, the proximal handle 375 is moved proximally to a first position 391 (FIG. 30A) where the internal shaft 310 locates the distal shield 380 to a first, proximal position 382. The first, proximal position 382 of the shield 380 covers the distal end 102 of the cannula 105 and seal system 103 of the invention. Once complete penetration of a body wall is confirmed, a spacer 390 may be removed that maintains a preferred storage relationship between the access device 100 and the placement device 300, then the proximal handle 375 may be urged forward to second position 391a (FIG. 30B) so that the internal shaft 310 moves the distal tapered, cone-shaped member 325 and the associated shield 380 forward to expose the distal end 120 of the cannula 105 and seal system 103. The placement device 300 is then moved through a third position 391b (FIG. 30C) as it is withdrawn from the cannula 105 and seal system 103.

Figure 31:
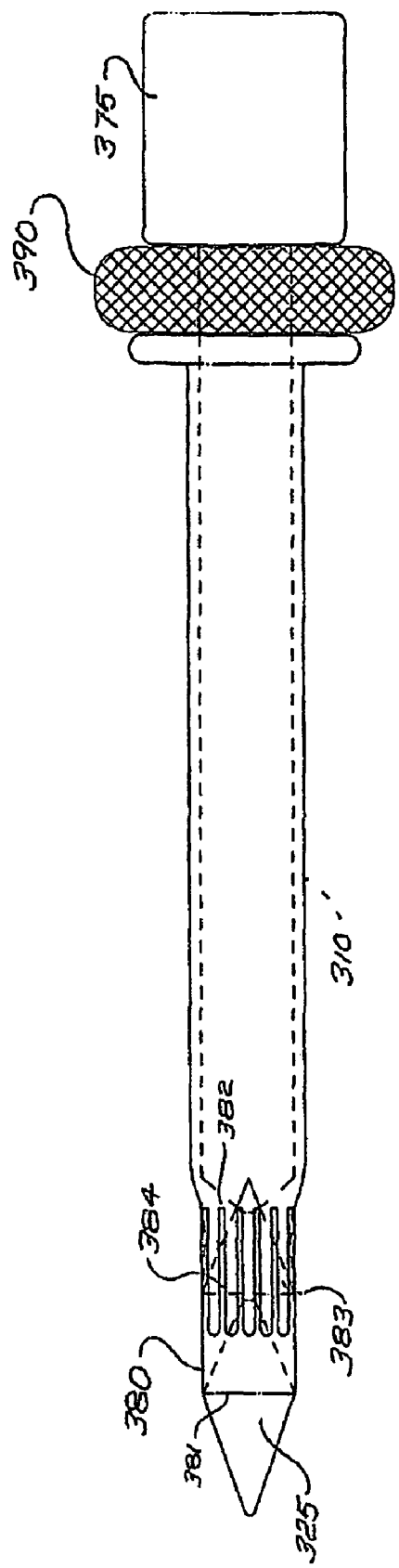
FIG. 31 illustrates a placement device for use in placing a laparoscopic cannula in accordance with another embodiment of the invention having a rigid and movable, collapsible shield.

FIG. 31 illustrates a placement device for use in placing a laparoscopic cannula in accordance with another embodiment of the invention having a rigid and movable, collapsible shield. In particular, FIG. 31 illustrates a placement device 300 having a distal shielding portion 380 that may be mechanically deployed and un-deployed. The mechanical shield 380 comprises a first conical portion 325 sized and configured to penetrate body tissue, a second portion that extends rearward to shield adjacent seal system 103 and a deployment member 310 sized and configured to move the shield from a deployed condition to an un-deployed condition. In one embodiment, shield 380 may comprise a cylinder having a distal end 381 connected to the proximal portion of the penetrating portion 325 at the widest region or largest diameter. The cylindrical shield 380 may be formed of a spring like material and further having axial slits 383 arranged around the circumference that may have a first, at rest, condition and a second condition under the influence of a deployment member. This embodiment contemplates that the spring-shield 380 covers the distal end 102 of the cannula-seal member 103 in a slightly compressed condition. The shield 380 is urged forward after penetration of body tissue is confirmed so that the shield moves from the shielding position and reduces in diameter so that it may be withdrawn from the cannula-seal 103.

The spring-shield comprises a cylinder that has a continuous circumference at a first end 381 and an interrupted circumference at a second end 382. The interrupted circumference resembles a plurality of extended fingers 384 extending from the continuous portion to the interrupted portion. The "at rest" condition of the interrupted portion may be configured so that the "fingers" 384 exhibit an inward bias toward the axis of the cylinder. The inward bias facilitates rearward removal of the shield 380 from the cannula-seal 103. A handle 375 associated with the proximal end 370 of the placement device 300 allows the user to selectively extend the distal end 320 of the placement device 300 beyond the distal end 102 of the cannula-seal 103 for removal.

Figure 32:
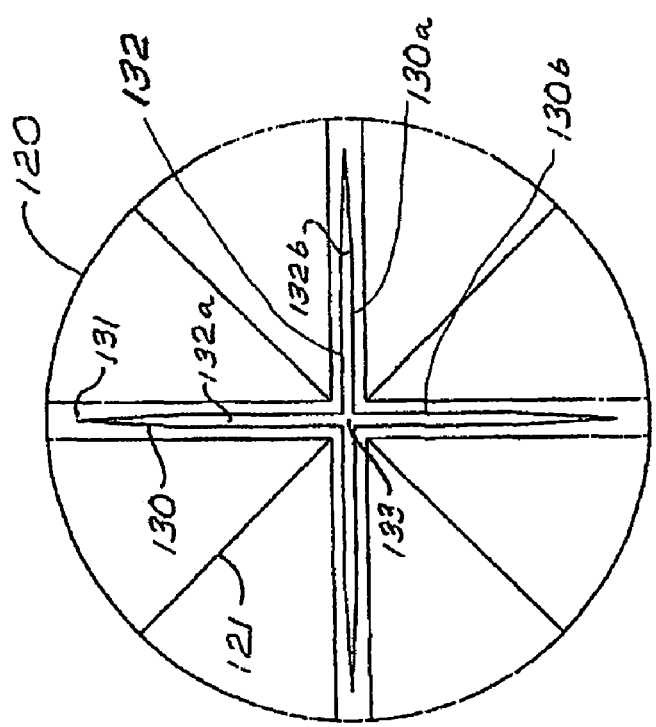
FIG. 32 illustrates a method for molding the open slits into a duckbill valve of the invention.

Referring to FIG. 32, a method for molding the open slits into a duckbill valve 120 is shown where a core that defines the shape and size of the interior of the valve 120 is supplied with, at least, a thin blade 132 which extends beyond the core for a distance. Additionally the thin blade 132 makes contact with a portion of the mold cavity 420 that describes and forms the exterior of the duckbill valve 120 so that the molded material is prevented from flowing to form a closure. The lateral edges 131 of the thin blade 132 are sharpened to a fine edge so that the molded material does not form in an area or shape that prevents full closure of the slits 130 on presentation of back-flow. In one embodiment of the invention, the duckbill valve 120 has two crossing slits 130a, 130b arranged at right angles in a single plane. This is commonly referred to as a double duckbill valve. The crossing slits 130a, 130b are normally cut into the molded material after the valve has been formed.

Figure 33:
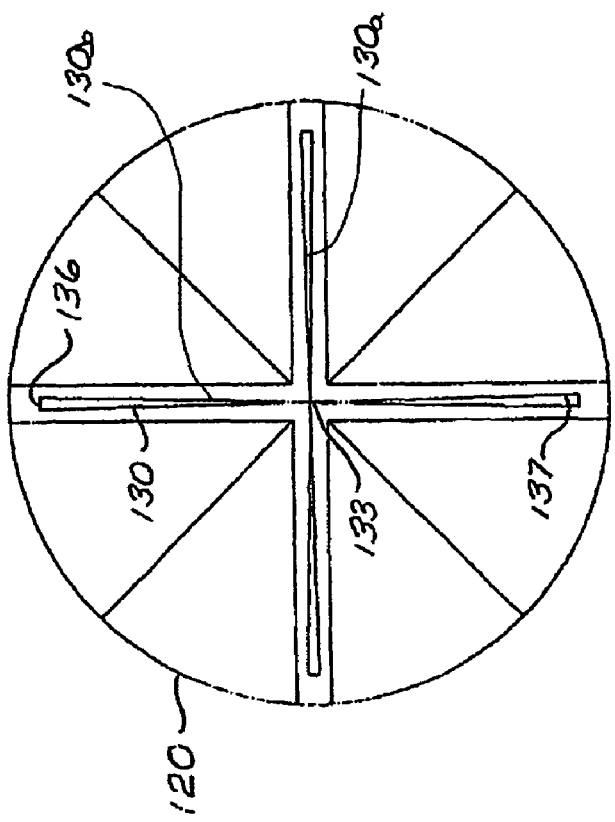
FIG. 33 illustrates another condition of the molded duckbill slit of the invention.

A method of manufacturing a double duckbill valve 120 comprises the insertion or placement of thin blades 132a, 132b or a thin-blade cross 133 at the sealing end of the valve mold core. The thin blades 132a, 132b or thin-blade cross 133 shut off the material flow during the molding process so that open slits are formed at the sealing end of the double duckbill valve 122. The lateral ends 131 are sharpened and slightly tapered so that there is no residual open portion 136 where the slits 130a, 130b terminate laterally. FIG. 33 shows the result of a condition where a residual opening 136 occurs in the molded valve 120. A thin blade 132 that is not sharpened at the lateral ends creates a non-sealing portion 136 where the blade or blades 132 terminate laterally.

Figure 34:
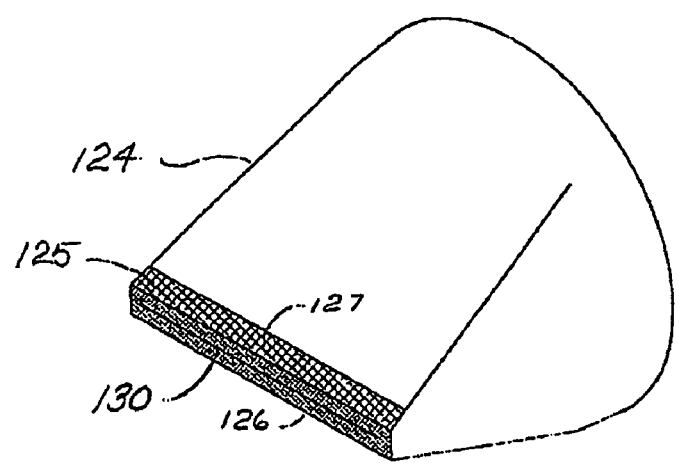
FIG. 34 illustrates another duckbill valve of the invention further comprising occlusive lip portions.
Figure 35:
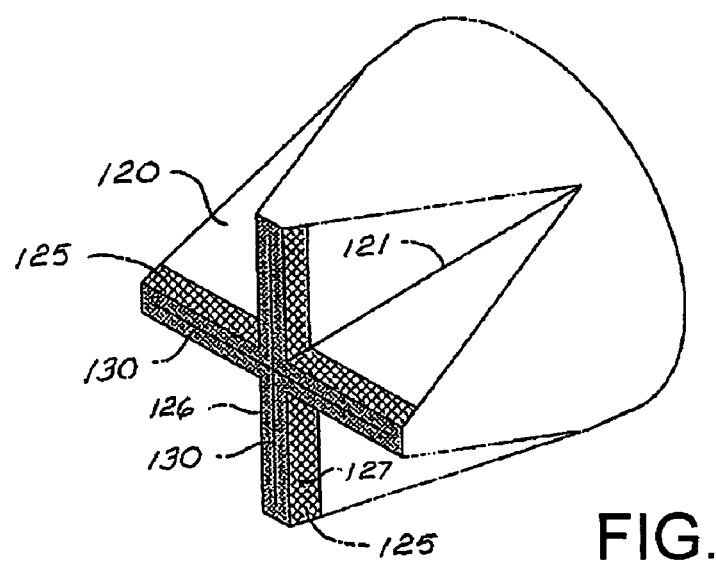
FIG. 35 illustrates a double duckbill of the invention further comprising occlusive lip portions.
Figure 36:
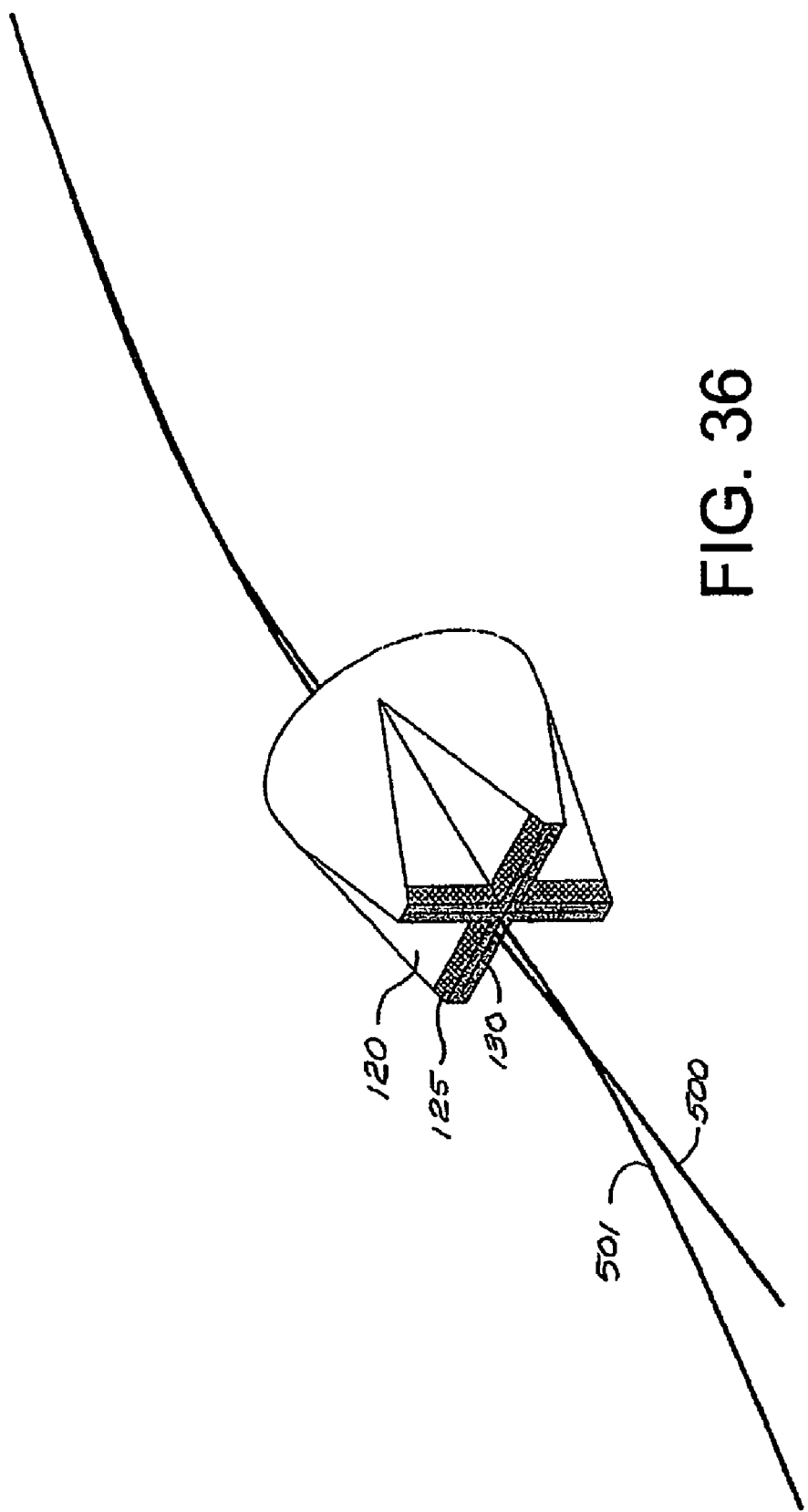
FIG. 36 illustrates suture extending through the double duckbill of the invention.
Figure 37:
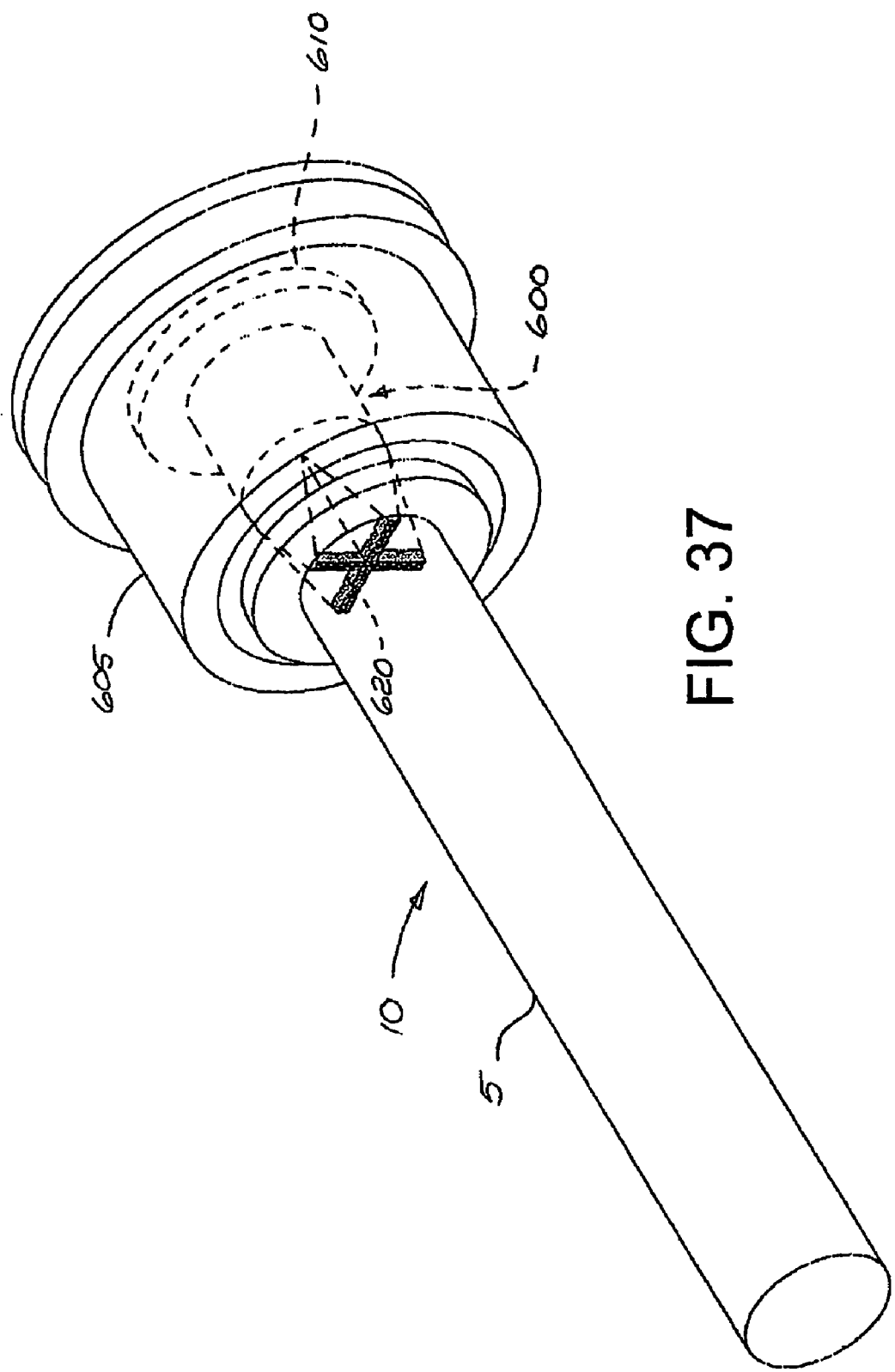
FIG. 37 is a perspective view of the double duckbill of the invention being incorporated within a rigid cannula and housing.
Figure 39:
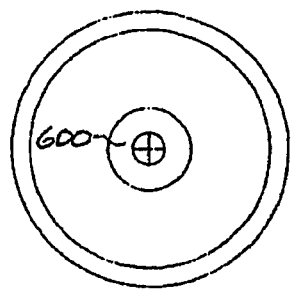
FIG. 39 is an end view of a rigid housing and cannula incorporating a self-sealing duckbill of the invention.
Figure 38:
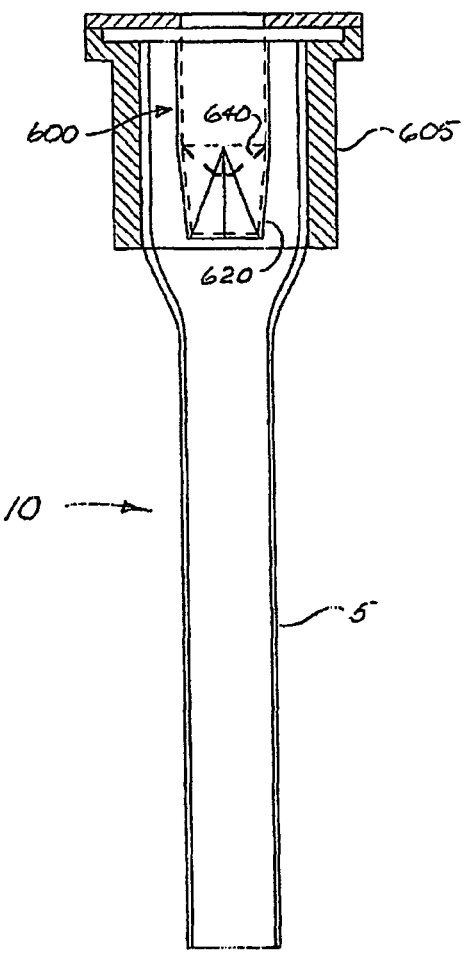
FIG. 38 is a side section view of a rigid housing and cannula incorporating a self-sealing duckbill of the invention.
Figure 40:
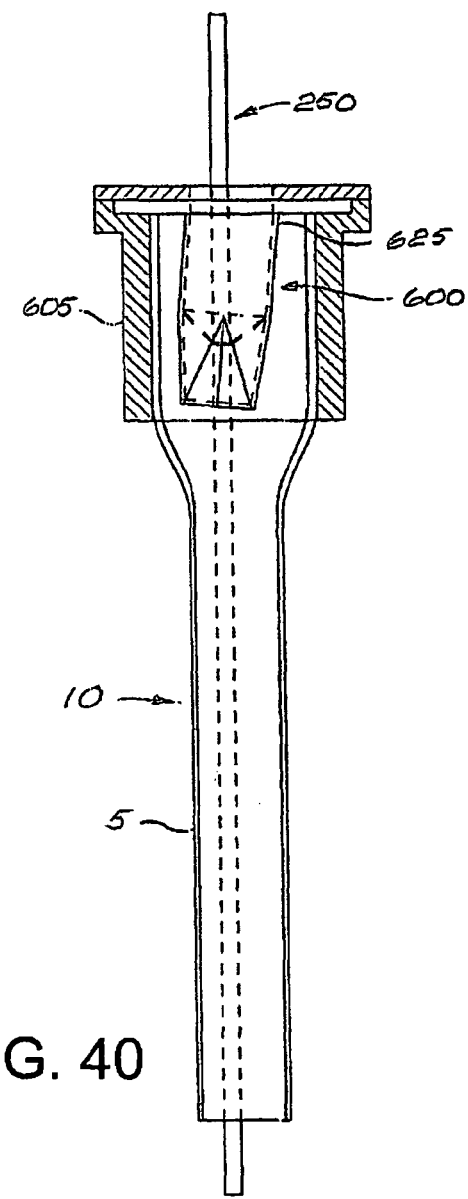
FIG. 40 is a side section view of a rigid housing and cannula incorporating a self-sealing duckbill of the invention with an instrument in place through the seal combination.
Figure 41B:
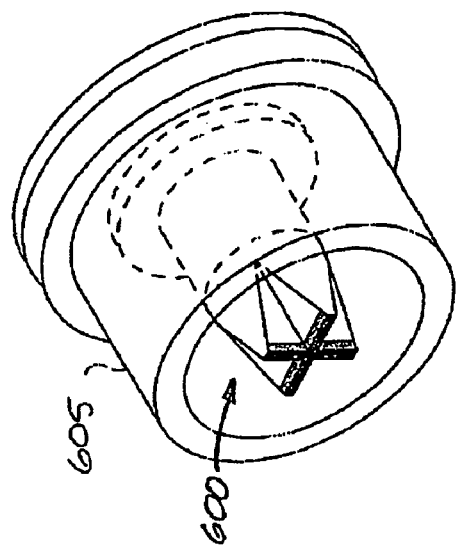
FIG. 41(B) is a perspective view of a self-sealing duckbill of the invention in an alternate embodiment as a seal module in use in a rigid housing.
Figure 41A:
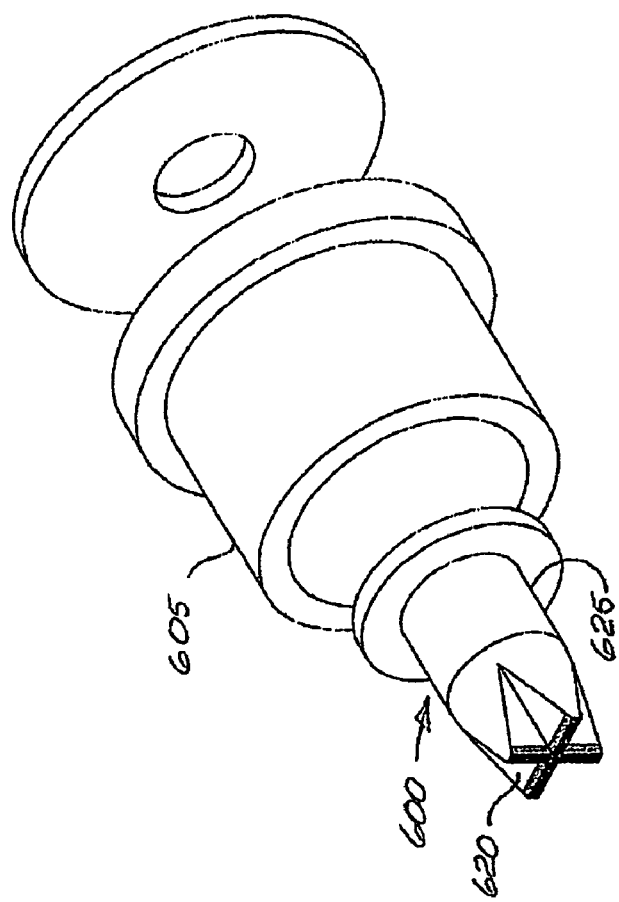
FIG. 41(A) is a perspective view of a self-sealing duckbill of the invention in an alternate embodiment as a seal module for use in a rigid housing.
Figure 42:
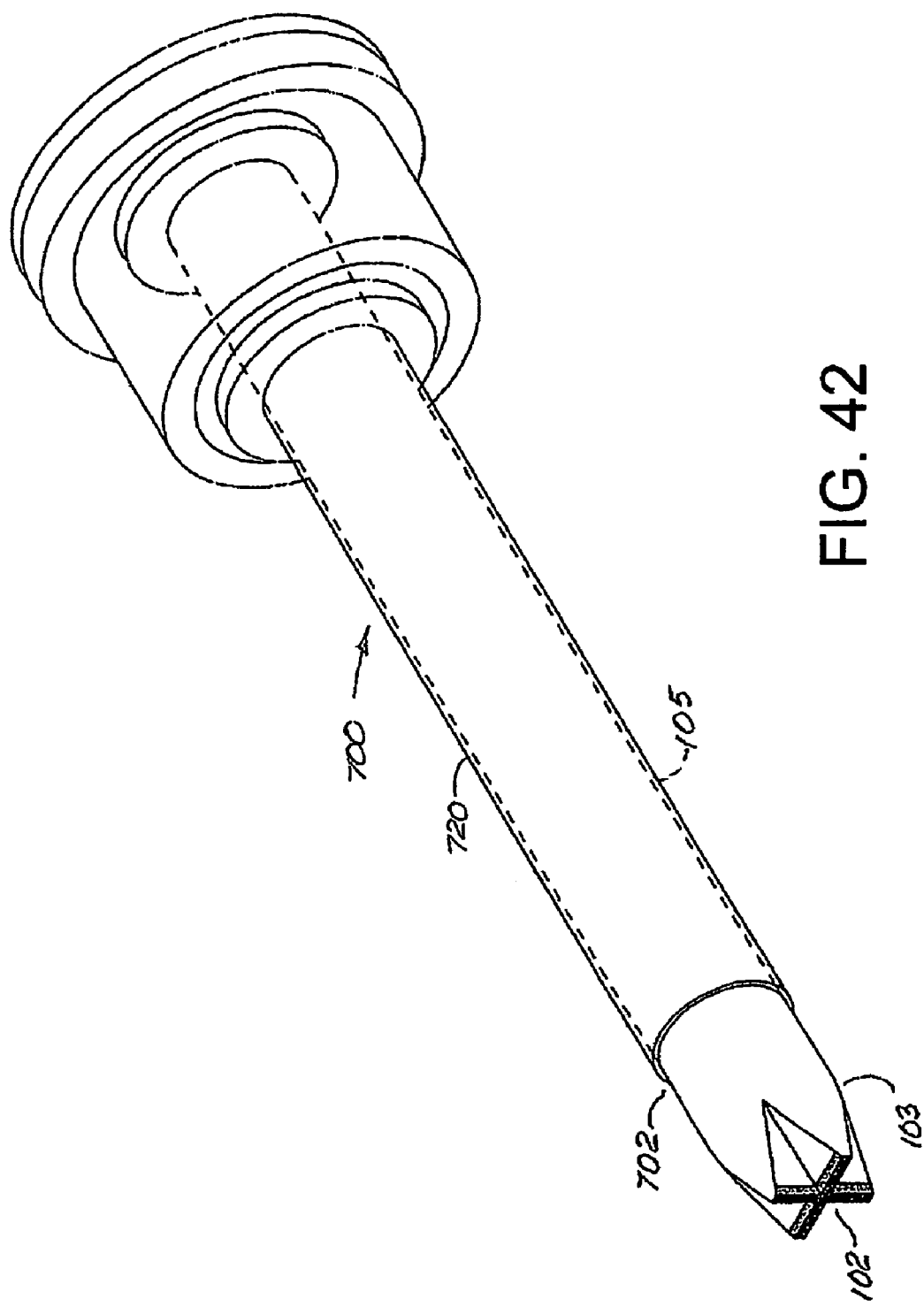
FIG. 42 is a perspective view of a self-sealing duckbill of the invention used within a standard trocar.

Referring to FIGS. 34, 35, duckbill valves 124, 120 are seen according to the present invention comprising opposing lip portions 126, 127 separated by slit portions 130. In this embodiment, the opposing lip portions 126, 127 are coated with or attached to a very soft and occlusive material 125. A material for the attached occlusive portions 125 may include silicone, KRATON®, Polyurethane or the like. The soft, occlusive portions 125 of the opposing lips 126, 127 of the duckbill seals 120, 124 allow the duckbill seals to form a complete seal while an object is within the sealing portions of the duckbill. Normally, duckbill seals only seal when there is no object extending through the sealing lip portions or slits 130. With the occlusive sealing lip portions 126, 127 of the invention, a user may extend selected items through the seal without disrupting the seal. For instance, FIG. 36 illustrates that a surgeon may be able to tie a suture knot extra corporeally without losing internal gas pressure during a laparoscopic surgery where the present invention is used as an access device. The suture extensions 500, 501 may extend through the duckbill seal 120 so that they can be tied and subsequently pushed into place through the access device 100. The occlusive material 125 associated with the slits 130 in the duckbill valve 120 allows the valve to close fully even while certain items 500, 501 remain in the fluid path of the valve 120.

With reference to FIGS. 37-41A, 41B, an alternate embodiment of the present invention is shown comprising a module 600 or combination of seal elements that are sized and configured to be used within a rigid seal housing 605 and cannula 5. This embodiment comprises a retaining portion 610, an extending portion 625, a first sealing portion 640 and a second sealing portion 620. The retaining portion 610 is sized and configured to fit within and be retained securely by a rigid seal housing 605. The extending portion 625 extends distally from the retaining portion 610 and preferably comprises a thin wall cylindrical structure or tube. A first seal 640 is associated with the distal end of the extending portion 625 that is sized and configured to receive a range of instruments there-through. A second seal 620 is associated with the distal portion of the first seal 640. The second seal is sized and configured to form a gas-tight zero seal. A module 600 or combination of seal elements constructed according to the present invention may be incorporated into a variety of rigid seal housings and provide the advantages of the present invention to otherwise deficient seal systems.

Additionally, a cannula and seal combination contemplates a flexible cannula 105 within, and co-axial to, a rigid cannula 720 associated with a standard access device 700 and where the seal combination 103 associated with the present invention extends beyond the distal end 702 of the rigid cannula 720 for a distance so as to allow the seal combination 103 to expand sufficiently to allow passage of instruments there-through. This configuration permits the use of the distal seal 103 in combination with a rigid cannula 720. Moreover, the rigid cannula 720 may be fitted over the flexible cannula 105 of the cannula and seal combination 100 of the present invention so that the features of the rigid cannula 720 may be utilized in combination with the advantages of the present invention.

It will be understood that many other modifications can be made to the various disclosed embodiments without departing from the spirit and scope of the invention. For these reasons, the above description should not be construed as limiting the invention, but should be interpreted as merely exemplary of preferred embodiments.

The invention claimed is:
1. A surgical access device, comprising:
an elongate tubular member having an outer surface, an inner surface, a working channel, and an axis extending between a proximal end and a distal end;
a septum seal integrally formed at the distal end of the tubular member, the septum seal comprising an elastomeric sheet having a frusto-conical shape and an orifice through the elastomeric sheet, the orifice configured to receive an instrument, and the frusto-conical shape extending from the inner surface of the tubular member radially inward to the orifice; and
a zero seal disposed at the distal end of the tubular member and distal to the septum seal, the zero seal being sized and configured to seal when no instrument is in place within the working channel of the tubular member, and the zero seal being coupled to the septum seal.

2. The surgical access device of claim 1, wherein the tubular member is formed from an elastomeric material.

3. The surgical access device of claim 1, wherein the zero seal is a duckbill seal constructed with an intersecting sealing portion.

4. The surgical access device of claim 3, wherein the duckbill seal comprises opposing lip portions separated by a slit portion.

5. The surgical access device of claim 4, wherein the opposing lip portions are coated with or attached to a soft or occlusive material providing back pressure forcing the lip portions to close even when the duckbill seal is slightly open.

6. The surgical access device of claim 5, wherein the occlusive material is one of silicone, KRATON®, and polyurethane.

7. The surgical access device of claim 5, wherein the opposing lip portions allow a surgical item to extend through the slit portion without disrupting a seal formed by the closure of the opposing lip portions.

8. The surgical access device of claim 7, wherein the surgical item is a surgical suture.

9. The surgical access device of claim 1, wherein the zero seal is a double duckbill seal constructed with two or more intersecting sealing portions.

10. The surgical access device of claim 1, further comprising a retaining portion at the proximal end of the tubular member.

11. The surgical access device of claim 10, wherein the retaining portion is a flange or a ring.

12. The surgical access device of claim 1, wherein the tubular member and the septum seal are molded together as a single unit.

13. The surgical access device of claim 12, wherein the zero seal is bonded, fused or over-molded with the septum seal.

14. The surgical access device of claim 1, wherein the tubular member, the septum seal and the zero seal are molded together or integrally formed as a single unit.

15. The surgical access device of claim 1, further comprising a placement device for placing the access device.

16. The surgical access device of claim 15, wherein the placement device is an obturator operable to pierce or penetrate tissue.

17. The surgical access device of claim 15, wherein the placement device includes an elongate shaft having a proximal end, a mid-portion and a distal end.

18. The surgical access device of claim 17, wherein the proximal end of the elongate shaft includes a handle sized and configured to be held by a user.

19. The surgical access device of claim 17, wherein the mid-portion of the elongate shaft has a reduced profile and is sized and configured to extend through the tubular member.

20. The surgical access device of claim 17, wherein the distal end of the elongate shaft is shaped like an hourglass.

21. The surgical access device of claim 17, wherein the distal end of the elongate shaft comprises a tapered, cone-shaped member.

22. The surgical access device of claim 1, wherein the orifice comprises a hole.

23. The surgical access device of claim 1, wherein the orifice comprises a piercing.

24. A surgical access device, comprising:
an elongate tubular member having an inner surface, an outer surface, a working channel, and an axis extending between a proximal end and a distal end;
a septum seal integrally formed at the distal end of the tubular member, the septum seal comprising an elastomeric sheet and an orifice through the elastomeric sheet, the orifice configured to receive an instrument; and
a duckbill valve positioned distal of the septum seal, the duckbill valve comprising:
opposing lip portions;
two crossing slits separating the opposing lip portions;
a plurality of folds formed in the outer surface of the tubular member at the distal end, each fold of the plurality of folds extending proximally from a distalmost extent of the access device; and
an occlusive material attached to the opposing lip portions.

25. The surgical access device of claim 24, wherein the occlusive material includes one of silicone, KRATON®, and polyurethane.

26. The surgical access device of claim 24, wherein the duckbill valve forms a complete seal with a selected item extending through the lip portions.

27. The surgical access device of claim 24, further comprising an enlarged retaining flange at the proximal end of the tubular member.

28. The surgical access device of claim 24, further comprising a bonding feature for attaching the septum seal to the duckbill valve.

29. A surgical access device, comprising:
an elongate tubular member having a working channel and an axis extending between a proximal end and a distal end; and
a seal system at the distal end of the tubular member, the seal system comprising:
a septum seal integrally formed with the tubular member, the septum seal comprising a septum having an orifice sized and configured to seal in conjunction with a specific range of usable instruments; and
a zero seal positioned at a distalmost extent of the surgical access device, coupled to the septum seal, and being sized and configured to seal the distalmost extent of the surgical access device to prevent backflow into the working channel when no instrument is in place within the working channel of the tubular member, and wherein the zero seal is coupled to the septum seal by bonding.

30. The surgical access device of claim 29, further comprising a bonding feature for attaching the septum seal to the zero seal.

31. A surgical access device, comprising:
an elongate tubular member having a working channel and an axis extending between a proximal end and a distal end; and
a seal system at the distal end of the tubular member, the seal system comprising:
a septum seal integrally formed with the tubular member, the septum seal comprising a septum having an orifice sized and configured to seal in conjunction with a specific range of usable instruments; and
a zero seal positioned at a distalmost extent of the surgical access device, coupled to the septum seal, and being sized and configured to seal the distalmost extent of the surgical access device to prevent backflow into the working channel when no instrument is in place within the working channel of the tubular member, and wherein the zero seal is coupled to the septum seal by fusing.

32. A surgical access device, comprising:
an elongate tubular member having a working channel and an axis extending between a proximal end and a distal end; and a seal system at the distal end of the tubular member, the seal system comprising:
   a septum seal integrally formed with the tubular member, the septum seal comprising a septum having an orifice sized and configured to seal in conjunction with a specific range of usable instruments; and
a zero seal positioned at a distalmost extent of the surgical access device, coupled to the septum seal, and being sized and configured to seal the distalmost extent of the surgical access device to prevent backflow into the working channel when no instrument is in place within the working channel of the tubular member, and wherein the septum comprises an elastomeric sheet having a frusto-conical shape.

* * * * *